(12) United States Patent
Keusenkothen et al.

(10) Patent No.: US 9,809,508 B2
(45) Date of Patent: *Nov. 7, 2017

(54) METHOD AND APPARATUS FOR CONVERTING HYDROCARBONS INTO OLEFINS

(75) Inventors: Paul F. Keusenkothen, Houston, TX (US); Frank Hershkowitz, Basking Ridge, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 721 days.

This patent is subject to a terminal disclaimer.

(21) Appl. No.: 13/994,220

(22) PCT Filed: Dec. 20, 2011

(86) PCT No.: PCT/US2011/066210
§ 371 (c)(1),
(2), (4) Date: Sep. 18, 2013

(87) PCT Pub. No.: WO2012/099679
PCT Pub. Date: Jul. 26, 2012

(65) Prior Publication Data
US 2014/0303416 A1    Oct. 9, 2014

Related U.S. Application Data

(60) Provisional application No. 61/434,419, filed on Jan. 19, 2011, provisional application No. 61/434,415, (Continued)

(30) Foreign Application Priority Data

Mar. 31, 2011  (EP) ..................................... 11160759

(51) Int. Cl.
C07C 5/09 (2006.01)
C07C 4/04 (2006.01)
(Continued)

(52) U.S. Cl.
CPC .................. *C07C 5/09* (2013.01); *C07C 2/06* (2013.01); *C07C 2/76* (2013.01); *C07C 4/04* (2013.01);
(Continued)

(58) Field of Classification Search
CPC ....................................................... C07C 5/09
(Continued)

(56) References Cited

U.S. PATENT DOCUMENTS 1,134,677 A    4/1915  Heinemann
1,860,624 A    5/1932  Sauerwein
(Continued)

FOREIGN PATENT DOCUMENTS

BE    722895    10/1968
DE    875198    4/1953
(Continued)

OTHER PUBLICATIONS

Olsvik, O.; Rokstad, O.A.; Holmen, A. "Pyrolysis of Methane in the Presence of Hydrogen", Chem. Eng. Technol. (1995), 18, pp. 349-358.*

(Continued)

*Primary Examiner* — In Suk Bullock
*Assistant Examiner* — Aaron Pierpont

(57) ABSTRACT

An apparatus and method are provided for processing hydrocarbon feeds. The method may pass a pyrolysis feed to a thermal pyrolysis reactor and expose at least a portion of the pyrolysis feed to high-severity operating conditions in a thermal pyrolysis reactor, wherein the thermal pyrolysis reactor is operated at operating conditions that include pressure ≥36 psig and provide a reactor product that has a $C_{3+}$ to $C_2$ unsaturate weight ratio ≤0.5.

16 Claims, 9 Drawing Sheets

Related U.S. Application Data filed on Jan. 19, 2011, provisional application No. 61/434,411, filed on Jan. 19, 2011, provisional application No. 61/434,417, filed on Jan. 19, 2011, provisional application No. 61/434,409, filed on Jan. 19, 2011, provisional application No. 61/434,413, filed on Jan. 19, 2011, provisional application No. 61/434,410, filed on Jan. 19, 2011, provisional application No. 61/481,999, filed on May 3, 2011, provisional application No. 61/500,854, filed on Jun. 24, 2011, provisional application No. 61/504,611, filed on Jul. 5, 2011.

(51) Int. Cl.

| | | |
|---|---|---|
| *C07C 2/06* | (2006.01) | |
| *C07C 2/76* | (2006.01) | |
| *C10G 47/00* | (2006.01) | |
| *C10G 9/00* | (2006.01) | |
| *C10G 9/18* | (2006.01) | |
| *C10G 9/20* | (2006.01) | |
| *C10G 9/26* | (2006.01) | |
| *C10G 50/00* | (2006.01) | |

(52) U.S. Cl.
CPC ............... *C10G 9/00* (2013.01); *C10G 9/002* (2013.01); *C10G 9/007* (2013.01); *C10G 9/18* (2013.01); *C10G 9/20* (2013.01); *C10G 9/26* (2013.01); *C10G 47/00* (2013.01); *C10G 50/00* (2013.01); *C10G 2300/4006* (2013.01); *C10G 2300/4012* (2013.01); *C10G 2300/42* (2013.01); *C10G 2400/20* (2013.01); *C10G 2400/22* (2013.01); *C10G 2400/24* (2013.01)

(58) Field of Classification Search
USPC ................. 585/251, 256, 501, 650; 422/187
See application file for complete search history.

(56) References Cited

U.S. PATENT DOCUMENTS

| | | | |
|---|---|---|---|
| 2,319,679 | A | 5/1943 | Hasche et al. |
| 2,678,339 | A | 5/1954 | Harris |
| 2,692,819 | A | 10/1954 | Hasche et al. |
| 2,852,440 | A * | 9/1958 | Smith ..................... C07C 11/02 |
| | | | 208/126 |
| 3,024,094 | A | 3/1962 | Coberly |
| 3,093,697 | A | 6/1963 | Kasbohm et al. |
| 3,156,733 | A | 11/1964 | Happel et al. |
| 3,242,223 | A | 3/1966 | Nonnenmacher et al. |
| 3,268,615 | A * | 8/1966 | Keenan, III ............... C07C 4/04 |
| | | | 585/635 |
| 3,419,632 | A | 12/1968 | Sogawa et al. |
| 3,617,495 | A | 11/1971 | Zimmerman, Jr. et al. |
| 3,644,555 | A | 2/1972 | Nagy et al. |
| 3,796,768 | A * | 3/1974 | Starzenski ............... B41J 25/24 |
| | | | 208/54 |
| 3,839,484 | A | 10/1974 | Zimmerman, Jr. et al. |
| 3,985,820 | A * | 10/1976 | Albright ............. B01J 19/2405 |
| | | | 201/2.5 |
| 4,274,841 | A | 6/1981 | Andresen et al. |
| 5,675,041 | A | 10/1997 | Kiss et al. |
| 5,856,592 | A | 1/1999 | Hagen |
| 6,049,011 | A | 4/2000 | Kiss et al. |
| 6,121,503 | A | 9/2000 | Janssen et al. |
| 6,177,600 | B1 | 1/2001 | Netzer |
| 6,210,561 | B1 | 4/2001 | Bradow et al. |
| 6,307,093 | B1 | 10/2001 | Godwin et al. |
| 6,578,378 | B2 | 6/2003 | Kaiser et al. |
| 7,045,670 | B2 | 5/2006 | Johnson et al. |
| 7,115,789 | B2 | 10/2006 | Kuechler et al. |
| 7,119,240 | B2 | 10/2006 | Hall et al. |
| 7,138,047 | B2 | 11/2006 | Stell et al. |
| 7,208,647 | B2 | 4/2007 | Peterson et al. |
| 7,491,250 | B2 | 2/2009 | Hershkowitz et al. |
| 7,815,873 | B2 | 10/2010 | Sankaranarayanan et al. |
| 7,846,401 | B2 | 12/2010 | Hershkowitz et al. |
| 7,943,808 | B2 | 5/2011 | Hershkowitz et al. |
| 8,158,837 | B2 | 4/2012 | Mamadov et al. |
| 8,440,070 | B2 | 5/2013 | Keusenkothen |
| 2002/0000085 | A1 * | 1/2002 | Hall et al. .................... 60/39.02 |
| 2002/0098430 | A1 | 7/2002 | Kawamura et al. |
| 2004/0002553 | A1 | 1/2004 | Hall et al. |
| 2004/0122267 | A1 * | 6/2004 | Sher ........................ C01B 3/38 |
| | | | 585/324 |
| 2004/0192982 | A1 | 9/2004 | Kuechler et al. |
| 2005/0065392 | A1 * | 3/2005 | Peterson .................. C07C 2/78 |
| | | | 585/324 |
| 2005/0096217 | A1 * | 5/2005 | Rokicki ................... B01J 23/62 |
| | | | 502/327 |
| 2007/0090018 | A1 | 4/2007 | Keusenkothen et al. |
| 2007/0090019 | A1 | 4/2007 | Keusenkothen et al. |
| 2007/0090020 | A1 | 4/2007 | Buchanan et al. |
| 2007/0191664 | A1 * | 8/2007 | Hershkowitz et al. ....... 585/539 |
| 2008/0142049 | A1 | 6/2008 | Onishi et al. |
| 2008/0300438 | A1 | 12/2008 | Keusenkothen et al. |
| 2010/0130803 | A1 | 5/2010 | Keusenkothen et al. |
| 2010/0292523 | A1 | 11/2010 | Hershkowitz et al. |

FOREIGN PATENT DOCUMENTS

| | | |
|---|---|---|
| DE | 1270537 | 6/1968 |
| DE | 2354217 | 5/1975 |
| EP | 1288182 | 3/2003 |
| EP | 1741691 | 1/2007 |
| EP | 2022772 | 2/2009 |
| GB | 795688 | 5/1958 |
| GB | 834419 | 5/1960 |
| GB | 846679 | 8/1960 |
| GB | 1007423 | 10/1965 |
| GB | 1090983 | 11/1967 |
| WO | 2005/097948 | 10/2005 |
| WO | 2011/008389 | 1/2011 |
| WO | 2012/099679 | 7/2012 |

OTHER PUBLICATIONS

Younessi-Sinaki, M.; Matida, E.A.; Hamdullahpur; F. "Kinetic model of homogeneous thermal decomposition of methane and ethane", International Journal of Hydrogen Energy, 34 (2009), pp. 3710-3716.*
Energy Fuels, 2007, 21(2), pp. 640-645.
Watt, L., "The Production of Acetlene from Methane by Partial Oxidation", Thesis University OG British Columbia, Sep. 1, 1951, pp. 1-50.
SRI Consulting Process Economics Program "Acetylene" Report 16 (1966) and 16A (1982).

* cited by examiner

METHOD AND APPARATUS FOR CONVERTING HYDROCARBONS INTO OLEFINS

CROSS-REFERENCE TO RELATED APPLICATIONS

This application claims priority from (i) U.S. Provisional Application Ser. No. 61/434,411, filed Jan. 19, 2011, EP Application No. 11160759.4, filed Mar. 31, 2011, and PCT/US2011/066210, filed Dec. 20, 2011; (ii) U.S. Provisional Application Ser. No. 61/434,409, filed Jan. 19, 2011, and PCT/US2011/066216, filed Dec. 20, 2011; (iii) U.S. Provisional Application Ser. No. 61/434,410, filed Jan. 19, 2011, and PCT/US2011/066202, filed Dec. 20, 2011; (iv) U.S. Provisional Application Ser. No. 61/434,413, filed Jan. 19, 2011, and PCT/US2011/066196, filed Dec. 20, 2011; (v) U.S. Provisional Application Ser. No. 61/434,415, filed Jan. 19, 2011, and PCT/US2011/066152, filed Dec. 20, 2011; (vi) U.S. Provisional Application Ser. No. 61/434,417, filed Jan. 19, 2011, and PCT/US2011/066186, filed Dec. 20, 2011; (vii) U.S. Provisional Application Ser. No. 61/434,419, filed Jan. 19, 2011, and PCT/US2011/066206, filed Dec. 20, 2011; (viii) U.S. Provisional Application Ser. No. 61/481,999, filed May 3, 2011, and PCT/US2011/066180, filed Dec. 20, 2011; (ix) U.S. Provisional Application Ser. No. 61/500,854, filed Jun. 24, 2011, and PCT/US2011/066174, filed Dec. 20, 2011; and (x) U.S. Provisional Application Ser. No. 61/504,611, filed Jul. 5, 2011, and PCT/US2011/066165, filed Dec. 20, 2011, the contents of each of which are incorporated by reference in their entirety.

FIELD

The present techniques relate to a method for converting hydrocarbons into olefins, such as ethylene, which may be further processed into the other products, such as polyolefins. Further, the present techniques relate to an apparatus used in the process, which enhances the conversion of hydrocarbons into olefins and other products.

BACKGROUND

The oil, gas and petrochemical industry desires to efficiently obtain hydrocarbons and process the hydrocarbons to produce desired products. Refining processes involve upgrading, converting or separating hydrocarbons (e.g., crude oil) into different streams, such as gases, light naphtha, heavy naphtha, kerosene, diesel, atmospheric gas oil, asphalt, petroleum coke and heavy hydrocarbons or fuel oil. Similarly, natural gas may be converted into industrial fuel gas, liquefied natural gas (LNG), ethane, propane, liquefied petroleum gas (LPG), and natural gas liquids (NGLs). The oil and gas processes are also often integrated with petrochemical systems to convert refinery streams into chemical products, such as ethylene, propylene or polyolefins.

To convert hydrocarbon feeds into petrochemical or basic chemicals, chemical conversion processes may be utilized. These processes typically involve using thermal or catalytic reactors or furnaces to produce reactive hydrocarbon products, such as acetylene, ethylene or propylene in different proportions. As an example, steam cracking reactors are commonly utilized to convert the hydrocarbon feed into ethylene and acetylene, which may be further processed into various chemical products. The steam cracking reactors are utilized because they provide feed flexibility by being able to utilize gas (e.g., ethane) and liquid (e.g., naphtha) feeds.

Historically, the oil and gas refineries utilize the higher value distillates from the hydrocarbon feed, which are typically fungible fuels, such as mogas, natural gas and diesel. As a result, the petrochemical refineries utilize the remaining fractions, such as ethane, propane, naphtha and virgin gas oil, in their processes. However, few chemical conversion processes are able to directly employ natural gas or the lower value refinery feeds, such as aromatic gas oils or fuel oils. As such, there is a need for a process that can produce ethylene and acetylene from different feeds, such as advantaged feeds (e.g., natural gas and/or aromatic gas oils).

To process these feeds, high-severity operating conditions (e.g., more severe operating conditions, such as higher temperatures) are generally involved to produce products having a higher value than the feed. High-severity operating conditions enable methane cracking and aromatic ring cracking, which do not occur at appreciable rates at typical low-severity conditions (e.g., conventional steam cracking conditions). At high-severity operating conditions, the primary products of thermal chemical conversion processes are acetylene and ethylene along with hydrogen ($H_2$) and coke, which may vary in proportion depending on the temperatures, pressures, residence times and feed type utilized. High-severity and low-severity conversion processes are typically based on different pyrolysis reactors, which may include pyrolysis alone or integrated with combustion chemistry. That is, the reactors may include pyrolysis chemistry (e.g., thermochemical decomposition of feed at elevated temperatures in the absence of oxygen) alone or in combination with combustion chemistry (i.e., exothermic chemical reactions between a feed and an oxidant). Although high-severity operating conditions may yield predominately acetylenes, acetylene may be further converted to ethylene and ultimately polyethylene or other derivatives using conventional technology. Conversion processes are typically based on different pyrolysis reactors. These pyrolysis reactors can be divided into different types: partial combustion that burns part of the pyrolysis feed, indirect combustion that involves contacting the pyrolysis feed with combustion products, are process that generate the electric arc or plasma to crack the pyrolysis feed, and thermal pyrolysis. Each of these pyrolysis types differs in the means of generating and transferring the heat for the pyrolysis, but can be broadly characterized as low-severity or high-severity.

Thermal pyrolysis reactors involve heating a solid material (e.g., by combustion) and using the heated solid material to crack the pyrolysis feed. In the thermal pyrolysis processes, the combustion products are typically maintained separate from the pyrolysis products or reactor effluent. This pyrolysis technique involves various different types of reactors, such as a furnace (e.g., as used in steam cracking), a regenerative reactor (e.g., as used in the Wulff process) and others. For instance, thermal pyrolysis is generally described in various references, such as U.S. Pat. Nos. 7,138,047 and 7,119,240. U.S. Pat. No. 7,119,240 describes an exemplary process for the conversion of natural gas into ethylene. In this process, natural gas is cracked in a furnace, actively quenched, and processed in a reactor to produce ethylene. As another example, U.S. Pat. No. 7,138,047 describes a steam cracking process that mixes a hydrocarbon feed with a dilution steam, flashing the mixture, and vaporizing a portion of the mixture in a pyrolysis reactor. In the process, the pyrolysis feed is passed through tubes in the radiant section of a thermal pyrolysis reactor to crack the pyrolysis feed without contaminating it with combustion products. However, due to the nature of a tubular (metal) furnace, steam cracking is limited to effective cracking temperatures of below 1000° C. and residence times of greater than or equal to (≥) 100 milliseconds (ms), which do not effectively convert either methane or aromatics, thereby limiting the feedstock selection. Pressures less than 50 pounds per square inch gauge (psig) (345 kiloPascal gauge (kPag)) are typically employed to maximize prime olefin yields (e.g., ethylene and propylene). In addition, energy or furnace heat not used in cracking is partially lost in the furnace flue gas or in the quench, as products are quickly cooled to stop undesired reactions.

The "Wulff" reactor, as described in the IHS, SRI Consulting's Process Economics Program "Acetylene" Report Number 16 (1966) and 16A (1982) along with U.S. Pat. Nos. 2,319,679; 2,678,339; 2,692,819; 3,024,094; and 3,093,697, uses a reverse-flow pyrolysis reactor, which is typically operated at temperatures of less than (<) 1400° C., to produce olefins and alkynes, such as acetylene. In addition, regenerative pyrolysis reactors are characterized as operating at pressures<15 psig (103 kPag). The pyrolysis feed is heated by refractories which have previously been heated by combustion reactions. The pyrolysis feed is cracked, and then further cooled outside of the reactor. The relatively slow quenching is a characteristic of the Wulff process that leads to coke and soot formation from using inefficient indirect heat transfer (e.g., from checker brick). Coke formation in the reactor provides fuel during the combustion cycle and excess coke or soot may be alleviated by using a light feed, i.e., a hydrocarbon containing a high proportion of hydrogen. However, because the indirect heat transfer limits the rate of heat input in the Wulff process, certain pyrolysis feeds, such as methane, may not be economically processed, which limits the feed flexibility for this process.

Further, while pyrolysis regenerative reactors have been used commercially, these reactors are not widely used for the conversion of certain feeds (e.g., natural gas or fuel oils) into acetylene or ethylene. That is, the inefficient refractories limit heat transfer (both for adding heat necessary for pyrolysis and for removing heat necessary for quenching). As a result, the Wulff reactors typically involve cracking temperatures below 1400° C. and involve the use of more expensive feeds, such as ethane, propane and naphtha. In addition, the poor heat transfer limits lead to greater soot generation resulting in poorer selectivity to desired products.

Moreover, various references describe that the reverse flow reactor is not feasible for converting methane to ethylene. In a comparison of the known acetylene conversion technologies, including the partial combustion, indirect combustion, arc processes, and thermal pyrolysis, the regenerative reactors are considered infeasible for methane to ethylene conversion due to the lower attainable temperatures in the Wulff process. That is, the Wulff process, which has checker bricks or refractory tiles within the reactor, is unable to withstand the constant temperature changes inherent in the process. Further certain of the references describe that partial oxidation of natural gas to acetylene with heat recovery is the most economical process. These references dismiss the use or lighter feeds, such as methane, because it can not be used economically. As such, the use of a reverse flow reactor is not taught as being possible for various reasons.

Although pyrolysis reactors may be used to convert hydrocarbons into useful products, such as acetylene and ethylene, improved reactions are desired which can make use of a broader range of feeds. Accordingly, it is desirable to provide a process that converts hydrocarbon feeds into conversion products, such as ethylene, in an enhanced manner. Further, it is desirable to manage the operating conditions (e.g., temperature and pressure) of the pyrolysis reactor to provide a process that converts hydrocarbon feeds into specific products in an enhanced manner.

SUMMARY

In one or more embodiments of the present techniques provides a method for enhancing the conversion of hydrocarbon feedstocks into propylene and/or ethylene. In particular, the present techniques utilize a regenerative pyrolysis reactor system to convert a hydrocarbon feed to ethylene, propylene and other petrochemical products in an enhanced manner.

In one or more embodiments, a hydrocarbon conversion method is described. The method comprising exposing a pyrolysis feed to thermal pyrolysis at a peak pyrolysis gas temperature ≥1200.0° C. and at a pressure ≥36 psig (248 kPag) to produce a reactor product that comprises $C_2$ unsaturates and has a $C_{3+}$ to $C_2$ unsaturate weight ratio ≤0.5.

In another embodiment, an apparatus for processing hydrocarbons is described. The apparatus comprises a thermal pyrolysis reactor configured to expose at least a portion of a pyrolysis feed to a peak pyrolysis gas temperature ≥1540.0° C. at a pressure ≥36 psig (248 kPag) within the thermal pyrolysis reactor to produce a reactor product comprising ethylene and acetylene and has a $C_{3+}$ to $C_2$ unsaturate weight ratio ≤0.5; a solid removal unit in fluid communication with the thermal pyrolysis reactor and configured to separate a bottoms product comprising tars and/or solids from at least a portion of the reactor product.

Further, in one or more embodiments, a method for processing hydrocarbons is described. The method comprises exposing a pyrolysis feed to thermal pyrolysis at a peak pyrolysis gas temperature ≥1200.0° C. and at pressure ≥36 psig (248 kPag) to produce a reactor product that comprises $C_2$ unsaturates and has a $C_{3+}$ to $C_2$ unsaturate weight ratio ≤0.5. The method may also include a conversion rate of greater than or equal to (≥) 20 wt % of the pyrolysis feed. Further, the method may involve a $C_{3+}$ to acetylene weight ratio ≤0.45, or ≤0.4, or ≤0.3, while the ethylene to acetylene weight ratio is ≥0.1 or ≥0.5. Further still, the method may include mixing other fluids, such as hydrogen, with the hydrocarbon feed to form a pyrolysis feed having a hydrogen gas to feed carbon molar ratio in the range of 0.1 to 5. In addition, the method may involve pressures ≥36 psig (248 kPag), or ≥44 psig (303 kPag) or ≥103 psig (710 kPag), but may be ≤300 psig (2068 kPag), or ≤163 psig (1124 kPag), or ≤150 psig (1034 kPag).

Further still, in one or more embodiments, an apparatus for processing hydrocarbons is described. The apparatus comprises a thermal pyrolysis reactor configured to expose at least a portion of a pyrolysis feed to a peak pyrolysis gas temperature equal to or above 1540° C. and at a pressure ≥36 psig (248 kPag) within the thermal pyrolysis reactor to produce a reactor product comprising ethylene and acetylene and a separation unit in fluid communication with the thermal pyrolysis reactor and configured to separate a bottoms product comprising tars and/or solids from at least a portion of the reactor product. The apparatus may further include an acetylene converter in fluid communication with the separation unit and configured to convert at least a portion of the reactor product into an ethylene product.

In certain embodiments of the method or apparatus, the thermal pyrolysis reactor may be a regenerative reverse flow reactor. This reactor may include a reactor body, wherein the reactor body forms a reaction region within the reactor body; a packing material disposed adjacent to the reaction region;

and valve means (e.g., one or more valve assemblies) coupled to the reactor body and in flow communication with the reaction region and configured to control fluid flow of the at least a portion of the pyrolysis feed between a location external to the reactor body and within the reaction region. Further, the one or more valve assemblies may be poppet valve assemblies.

In certain embodiments of the method or apparatus, the high-severity operating conditions may include exposing the pyrolysis feed to a peak pyrolysis gas temperature from 1540.0° C. to 2200.0° C., and the residence time for the at least a portion of the pyrolysis feed within the thermal pyrolysis reactor is between 0.5 second and 0.001 second. In other embodiments, the high-severity operating conditions may include exposing the pyrolysis feed to a peak pyrolysis gas temperatures from 1600.0° C. to 1800.0° C., and the residence time for the at least a portion of the pyrolysis feed within the thermal pyrolysis reactor in the range of 0.5 seconds and 0.001 seconds. The method may involve a cycle time of a combustion step (e.g., combustion) and a pyrolysis step (e.g., pyrolysis) that is between 0.5 second to 30 seconds.

Figure 1A:
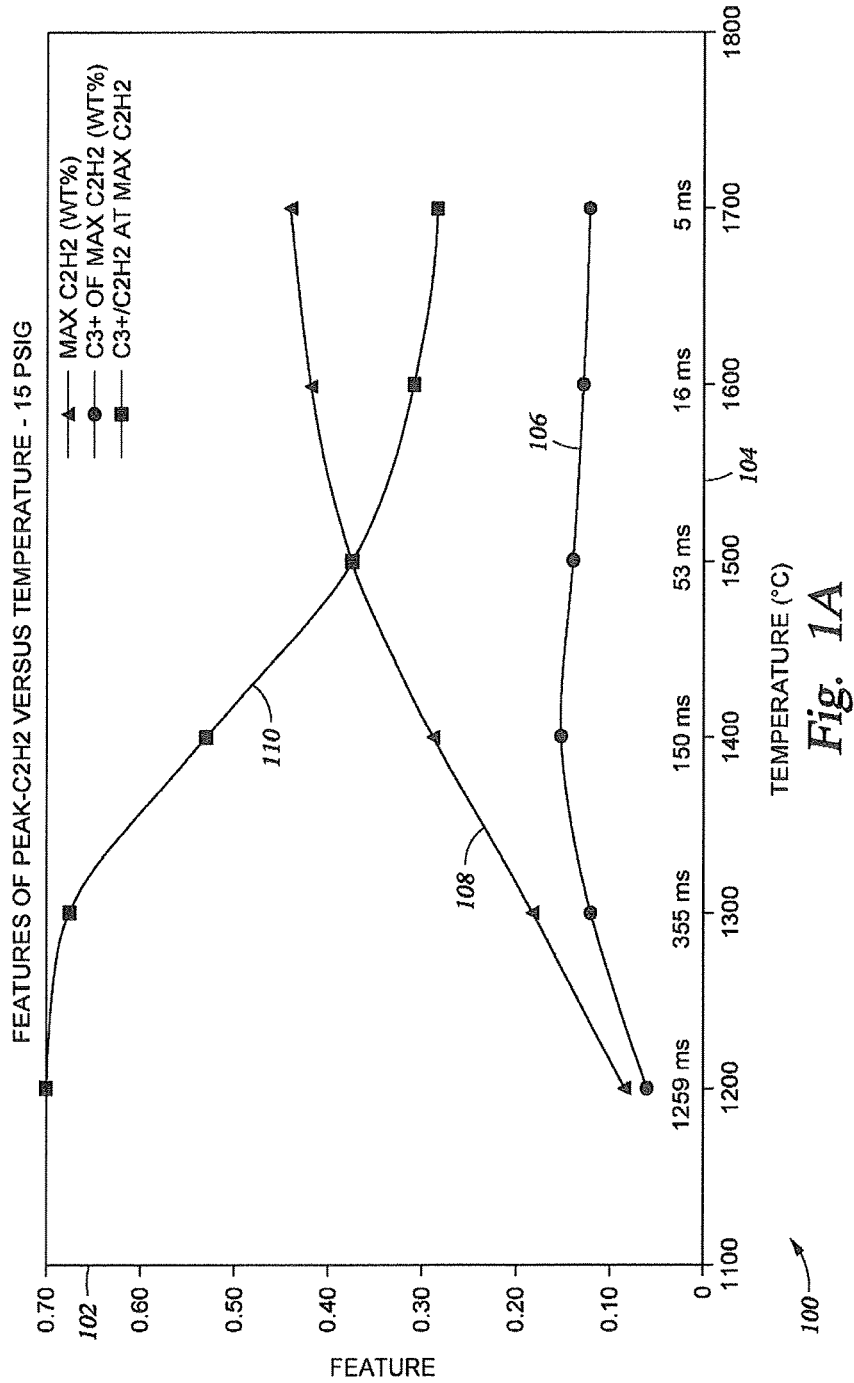
FIGS. 1A to 1F are diagrams of simulation results representing different ratios of reactor products produced at different temperatures and/or different pressures.

Although the invention is described in terms of a thermal pyrolysis process for producing acetylene and ethylene, the invention is not limited thereto. To the extent that the following detailed description is specific to a particular embodiment or a particular use, this is intended to be illustrative only, and is not to be construed as limiting the scope of the invention. The invention is intended to cover all alternatives, modifications and equivalents that may be included within the spirit and scope of the invention, as defined by the appended claims.

DETAILED DESCRIPTION OF THE EMBODIMENTS

In contrast to conventional techniques, the present techniques provide an enhanced process for conversion of feed containing hydrocarbons to acetylene and ethylene and optionally polyethylene. The present techniques utilize a thermal pyrolysis reactor configured to expose the pyrolysis feed to higher temperatures than conventional steam cracking. These higher temperatures are utilized to crack feeds that are normally unreactive or react to low value products (e.g., degraded products) at lower temperatures. As a specific example, at temperatures≥1200.0° C., methane and aromatic components are partially cracked to yield unsaturated $C_2$+ compounds, typically acetylenes and ethylene. At temperatures≥1400.0° C. or preferably ≥1540.0° C., aromatics and methane may be cracked at high conversion levels, with selectivity levels≥50 wt % to light gas products. That is, at atmospheric pressure, higher temperature also provides selectivity to enhance the yield of unsaturated $C_2$+ compounds (e.g., yield of ethylene and acetylene). For example, the ethylene to acetylene weight ratio (E/A) can be ≤0.10 or as low as 0.02 at atmospheric pressure.

To further enhance the process, as noted below, higher pressure may be utilized to increase the E/A for certain operating conditions. The present techniques utilize a thermal pyrolysis reactor configured to expose the pyrolysis feed to higher pressures than conventional thermal pyrolysis processes. These higher pressures are utilized to crack feeds at higher temperatures to yield higher conversions and selectivities to ethylene. As a specific example, at pressures ≥36 psig (at peak pyrolysis gas temperatures≥1500° C.), methane and aromatic components are partially cracked to yield elevated levels of ethylene relative to lower pressures.

At any elevated temperature, hydrocarbon pyrolysis or hydropyrolysis produces acetylene at an intermediate residence time. As time continues, the hydrocarbons react further towards condensed species and eventually carbon (e.g., produce more coke). Thus, there is a maximum amount of acetylene, which is achieved at a specific residence time, and which is the optimum acetylene yield for a given temperature. The temperature and residence time of this maximum acetylene yield can be used to characterize thermal pyrolysis reactor performance at that temperature, in terms of the yield of $C_{3+}$ in relationship to the yield of acetylene. The yield of $C_{3+}$, as used herein, includes all $C_{3+}$ products of the pyrolysis feed, whether those products emerge from the reactor or remain within the reactor as coke. $C_{3+}$ includes, for example, products such as methyl acetylene, benzene and tar, and is specifically defined as including carbonaceous byproducts, such as coke.

To further explain the high-severity pyrolysis reactor and its associated products, various simulation results representing different ratios of reactor products produced at different temperatures and/or different pressures are provided. These simulations utilize certain feeds, such as methane, for simplicity, but the invention is not limited thereto. The maximum acetylene yield, the corresponding $C_{3+}$ yield and the acetylene to $C_{3+}$ weight ratio are described further in relation to temperature and residence time in FIGS. 1A and 1B and Table 1.

Figure 1B:
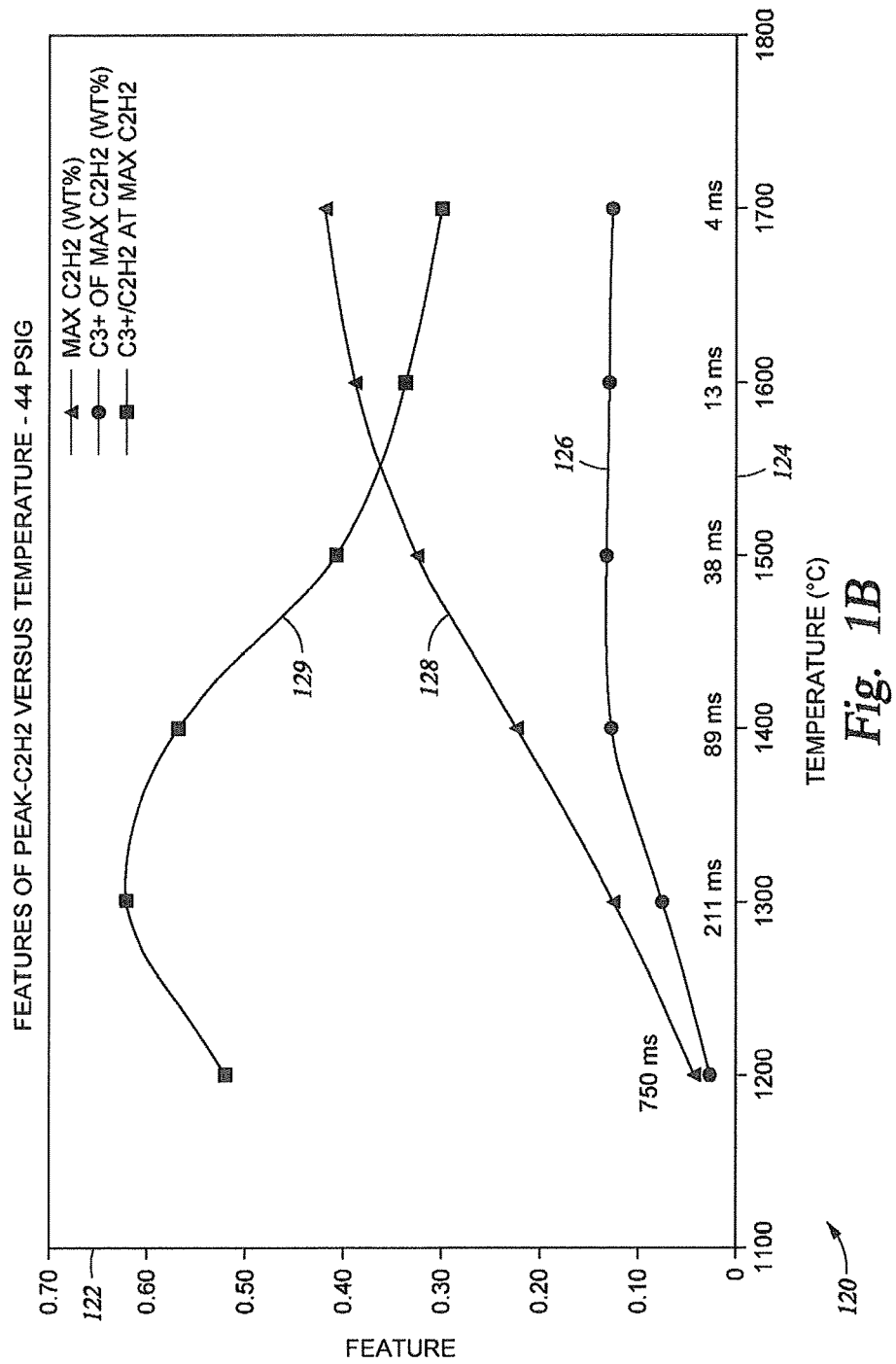

FIGS. 1A and 1B illustrate the simulation results for different ratios of reactor products produced at different temperatures from a methane feed. The consequences of operating at various temperatures are provided for comparison of the product yields achievable at the residence time associated with the maximum acetylene yield for that temperature. Pyrolysis, in this example, is carried out under isothermal conditions, with 2:1 molar diluent of hydrogen in a methane feed, and at a pressure of 14.7 psig (101 kPag) for diagram 100 and at a pressure of 44 psig (303 kPag) for diagram 120. All hydrocarbon products larger than $C_2$ are considered as $C_{3+}$ in this example and the product is the reaction product yield from the converted pyrolysis feed. In diagram 100, certain values for maximum acetylene yield 108 in weight percent (wt %) of the product, and corresponding $C_{3+}$ yield 106 in wt % of the product, and $C_{3+}$ to acetylene weight ratio 110 of the product are shown along the Y-axis 102 for various temperatures (in ° C.) along the X-axis 104. The $C_{3+}$ to acetylene weight ratio 110 has a peak between the temperatures of 1200° C. and 1400° C., which decreases at a slower rate as temperature increases from 1500° C. or 1540° C. Similarly, in diagram 120, certain values for a maximum acetylene yield 128 in wt % of the product, and corresponding $C_{3+}$ yield 126 in wt % of the product and $C_{3+}$ to acetylene weight ratio 129 of the product are shown along the Y-axis 122 for various temperatures (in ° C.) along the X-axis 124. The $C_{3+}$ to acetylene weight ratio 110 again has a peak within the range of 1300° C. to 1400° C., which decreases at a slower rate from 1500° C. or 1540° C. as the temperature increases. As such, operating conditions of the thermal pyrolysis reactor may be adjusted to enhance the acetylene yield for a pyrolysis feed.

This aspect is further described in Table 1, which includes simulation results for different ratios of reactor products produced at different temperatures from methane. The consequences of operating at various temperatures are provided for comparison of the product yields achievable at the residence time associated with the maximum acetylene yield for that temperature. Pyrolysis, in this example, is carried out under isothermal conditions, with 2:1 molar diluent of hydrogen (as $H_2$) in a methane feed, and at 14.7 psig (101 kPag) reactor pressure. Table 1 lists the results, such as composition of the pyrolysis product (weight percent of total pyrolysis product), for operations at temperatures between 1200° C. and 2200° C.:

TABLE 1

| | Temperature (° C.) | | | | | | | | |
|---|---|---|---|---|---|---|---|---|---|
| | 1200 | 1300 | 1400 | 1500 | 1540 | 1600 | 1650 | 1700 | 2200 |
| Max $C_2H_2$ (wt % of product) | 8.6% | 18.1% | 28.8% | 37.5% | 39.6% | 41.8% | 43.0% | 44.0% | 49.4% |
| Time of max $C_2H_2$ (sec) | 1.259 | 0.355 | 0.150 | 0.053 | 0.035 | 0.016 | 0.009 | 0.005 | 0.00006 |
| $C_{3+}$ (wt % of product) | 6.0% | 12.2% | 15.3% | 14.0% | 13.7% | 12.9% | 12.6% | 12.3% | 12.9% |
| $C_{3+}/C_2H_2$ | 0.699 | 0.673 | 0.530 | 0.372 | 0.346 | 0.308 | 0.293 | 0.281 | 0.261 |
| $C_2H_2$/unit reactor volume (relative units) | 0.068 | 0.510 | 1.928 | 7.066 | 11.31 | 26.38 | 47.8 | 92.98 | 8233 |
| $CH_4$ conversion | 29.9% | 53.4% | 73.3% | 83.1% | 84.6% | 86.9% | 88.8% | 88.7% | 96.9% |
| $H_2$ (wt % of product) | 24.2% | 27.9% | 31.2% | 32.9% | 33.2% | 33.6% | 34.0% | 33.9% | 34.8% |
| Surplus $H_2$ (wt % of prod.) | 3.5% | 6.5% | 8.9% | 10.0% | 10.1% | 10.3% | 10.6% | 10.4% | 11.0% |

As shown in this table, the maximum acetylene yield increases rapidly with temperature until 1500° C. Above this temperature, the maximum acetylene yield increases at a slower rate. Further, the residence time required to achieve this conversion decreases with increasing temperature. For instance, at 1200° C., residence times over 1 second are needed, and acetylene comprises only about 8.6 wt % of the products, while at 1700° C., residence times of about 5 milliseconds are needed and acetylene comprises 44.0 wt % of the products. Residence time has a large impact on reactor volume (proportional to the reciprocal of residence time). As a result, a given unit of reactor may process more pyrolysis feed when the reactor temperature is high and residence time is low. However, the very short residence times that achieve optimal acetylene yields at very high temperatures may place demands on certain reactor components that may exceed practicality. For example, where the pyrolysis feed is being flowed through the hot region of the pyrolysis reactor, the required gas velocity is roughly equal to the length of the hot region divided by the desired residence time. Gas velocities in flow channels and valve orifices are preferred to be less than the velocity of sound, which may result in reactor lengths that are not practical. In addition, because thermal pyrolysis involves the transfer of heat through a solid intermediary from a combustion step to a pyrolysis step, extremely short residence times may impose a heat transfer rate requirement (heat of reaction divided by reaction time) that may not be practical. As such, the design and operating conditions of the reactor may limit the maximum temperature that may be utilized to crack the pyrolysis feed.

Even though maximum acetylene ($C_2H_2$) yield increases for methane with increasing temperature, the $C_{3+}$ yield is greatest for intermediate temperatures, such as 1400° C. Dividing $C_{3+}$ yield by acetylene yield gives a selectivity parameter ($C_{3+}/C_2H_2$) that indicates how much $C_{3+}$, which is related to coke production, has to be managed per unit of acetylene produced. This selectivity parameter remains very high (e.g., ≥0.5) for temperatures below 1500° C., and drops into a lower section (e.g., ≤0.45 or ≤0.4) for temperatures at or above 1500° C.

For feeds containing high levels of aromatics or methane, temperatures below 1500° C. are not as effective for production of acetylene because of the high $C_{3+}$ yields, the low acetylene yields, and the relatively long residence times (e.g., large reactor volumes) needed for processing. Conversely, considering the broad range of temperature cited for methane pyrolysis, there is an advantage to operating at temperatures above 1500° C., in terms of $C_2U$ yield and $C_2$ selectivity.

While the high-severity temperatures may be preferred if the objective of the process is to produce acetylene, variations in pressure along with the high-severity temperatures may enhance the distribution of $C_2$ compounds (e.g., yield of ethane, ethylene and acetylene) and the distribution of other light hydrocarbons (e.g., propylene, propyne, etc.). Accordingly, these pressure variations may be utilized if ethylene and/or other olefins are the preferred product. As an example, steam cracking typically utilizes lower temperature to convert ethane to ethylene and trace levels of acetylene. At atmospheric pressure, lower temperatures result in higher ethylene to acetylene (E/A) weight ratios. However, lower temperatures also provide poor conversions for methane and aromatics, which as noted above, is inefficient. At high-severity conditions (e.g., temperatures ≥1400° C. or preferably ≥1540° C., for example) aromatics and methane may be cracked at high conversion levels, with selectivity levels ≥50 wt % to light gas products. Also shown in Table 1, at temperatures ≥1400° C., selectivity levels ≥50 wt % to light gas products are achievable. For example, at 1540° C., products of methane make up 67.8 wt % of the pyrolysis product, including $H_2$, $C_2$'s, and $C_{3+}$. Thus, the selectivity to $C_{3+}$ is 20 wt % (13.7 wt %/67.8 wt %), and the selectivity to lighter gas products is 80 wt %. Further, by varying the pressure from atmospheric to elevated pressures (e.g., up to 300 psig (2068 kPag)), ethylene to acetylene (E/A) weight ratios ≥0.1, or ≥0.2, or ≥0.4 or even ≥0.5 may be achieved. The variations of pressure at high-severity operating conditions are described below in Tables 2 and 3 and FIGS. 1C to 1F.

Table 2 includes simulation results for different ratios of reactor products produced at different pressures for different temperatures from a methane feed. Pyrolysis, in this example, is carried out under isothermal conditions at 1500° C. and at 1650° C., with 2:1 molar diluent of hydrogen in a methane feed, and at 15 psig (103 kPag) reactor pressure to 162 psig (1117 kPag) reactor pressure. All products larger than C2 are considered as $C_{3+}$ in this example and the product is the reaction product yield from the converted pyrolysis feed.

TABLE 2

70% Isothermal Conversion Data

| Temp (° C.) | P (psig) | Time (sec) | Conv. | Products (weight percent) | | | | | $C_2U$ | $C_{3+}/C_2U$ | E/A |
|---|---|---|---|---|---|---|---|---|---|---|---|
| | | | | $H_2$ | $CH_4$ | $C_2H_2$ | $C_2H_4$ | $C_{3+}$ | | | |
| 1500 | 15 | 0.025 | 72% | 31.1 | 22.0 | 34.2 | 2.0 | 10.7 | 36.0 | 0.30 | 0.06 |
| 1500 | 36 | 0.025 | 73% | 31.1 | 21.7 | 32.7 | 3.1 | 11.3 | 36.0 | 0.32 | 0.10 |
| 1500 | 44 | 0.025 | 72% | 31.0 | 22.1 | 31.9 | 3.5 | 11.5 | 35.0 | 0.33 | 0.11 |
| 1500 | 59 | 0.025 | 71% | 30.7 | 23.3 | 30.3 | 4.1 | 11.6 | 34.0 | 0.34 | 0.14 |
| 1500 | 74 | 0.025 | 69% | 30.4 | 24.7 | 28.6 | 4.6 | 11.7 | 33.0 | 0.35 | 0.16 |
| 1500 | 103 | 0.025 | 65% | 29.7 | 27.9 | 25.4 | 5.4 | 11.5 | 31.0 | 0.37 | 0.21 |
| 1500 | 162 | 0.025 | 57% | 28.4 | 34.3 | 20.3 | 6.3 | 10.8 | 27.0 | 0.41 | 0.31 |
| 1650 | 15 | 0.0025 | 68% | 30.4 | 25.4 | 35.0 | 1.0 | 8.2 | 36.0 | 0.23 | 0.03 |
| 1650 | 36 | 0.0025 | 71% | 30.8 | 23.6 | 35.6 | 1.5 | 8.5 | 37.0 | 0.23 | 0.04 |
| 1650 | 44 | 0.0025 | 71% | 30.8 | 23.3 | 35.6 | 1.7 | 8.6 | 37.0 | 0.23 | 0.05 |
| 1650 | 59 | 0.0025 | 71% | 30.9 | 22.9 | 35.4 | 2.0 | 8.7 | 37.0 | 0.23 | 0.06 |
| 1650 | 74 | 0.0025 | 71% | 30.9 | 22.8 | 35.2 | 2.3 | 8.8 | 37.0 | 0.24 | 0.07 |
| 1650 | 103 | 0.0025 | 71% | 30.8 | 22.9 | 34.4 | 3.0 | 8.9 | 37.0 | 0.24 | 0.09 |
| 1650 | 162 | 0.0025 | 70% | 30.5 | 24.0 | 32.5 | 4.1 | 9.0 | 37.0 | 0.25 | 0.13 |

As shown in Table 2, as pressure increases from 15 psig (103 kPag) to 162 psig (1117 kPag), $C_2U$ yields in wt % of the product are roughly constant at about 33 wt % (+/−10 wt %) for 25 millisecond (ms) residence time at 1500° C. However, the E/A weight ratios improve over this increase in pressure. At 1650° C., the $C_2U$ yields in wt % of the product are again roughly constant at about 37 wt % (+/−10 wt %) for 2.5 ms, while the E/A weight ratio increases fourfold. Accordingly, the higher pressures tend to lead to higher E/A weight ratios. Further, the $C_{3+}$ yields in wt % of the product at these different temperatures and pressures also remain relatively constant at 12% for 1500° C. and 9% for 1650° C. As a result, the $C_{3+}$ to $C_2U$ weight ratio ($C_{3+}/C2U$) increases at slow rate with pressure at the lower temperature, while the higher temperatures provide a roughly constant $C_{3+}$ to $C_2$ unsaturate weight ratio.

From this table, the yield of $C_2U$ (e.g., acetylene and ethylene) may be optimized for certain operating conditions. That is, a specific pressure, temperature and residence time may be utilized to optimize the distribution of $C_2U$ yield. These operating conditions may be characterized by the $C_{3+}$ to $C_2U$ weight ratio along with an E/A weight ratio, which may be further explained in view of the FIGS. 1C and 1D.

Figure 1C:
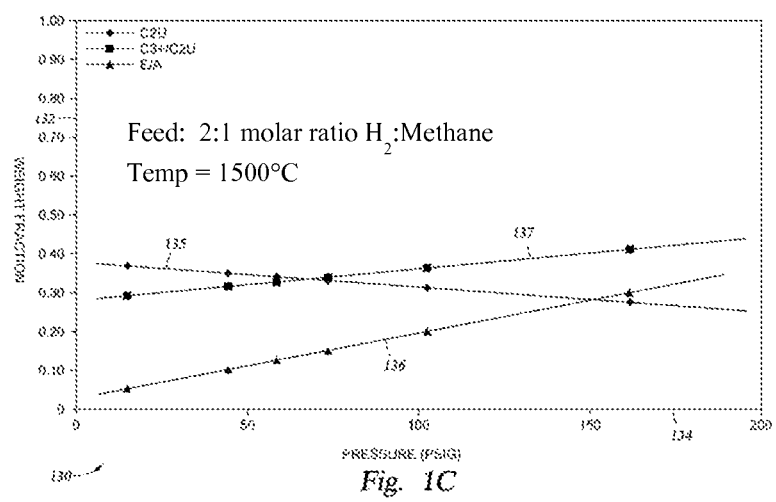
Figure 1D:
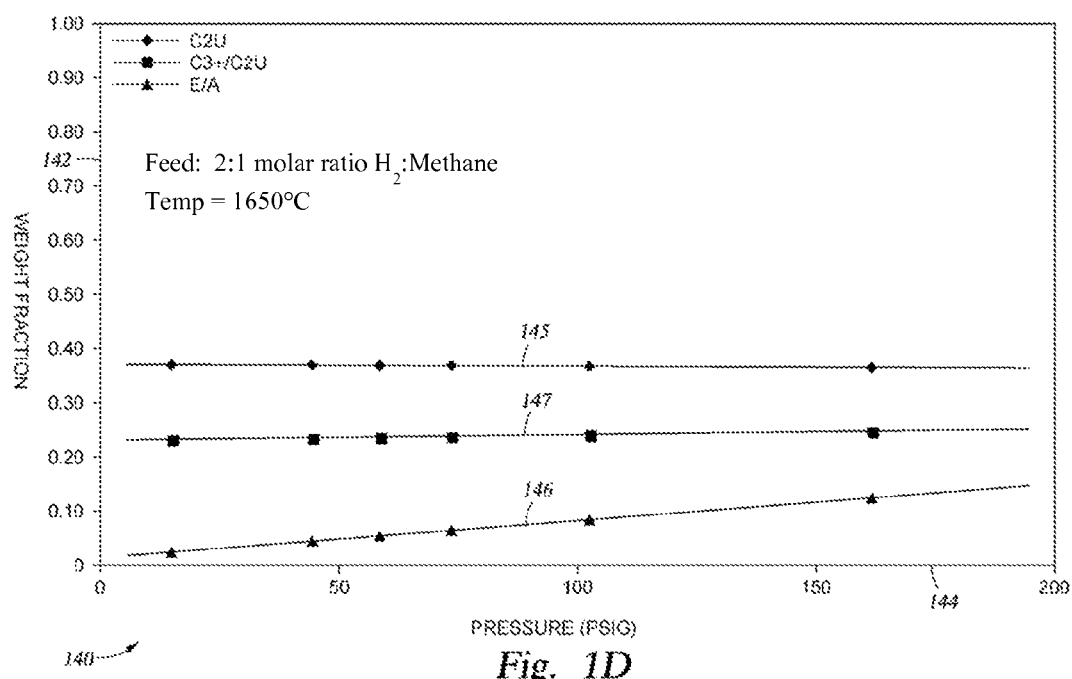

FIGS. 1C and 1D illustrate the simulation results for different ratios of reactor products produced at different pressures for certain temperatures from methane. The results of operating at the various pressures are provided for comparison of the product yields achievable at the residence times associated with the $C_2U$ yield and an E/A weight ratio for that pressure. Pyrolysis, in this example, is carried out under isothermal conditions, with 2:1 molar diluent of hydrogen in a methane feed, and at 1500° C. for diagram 130 and at 1650° C. for diagram 140. All products larger than $C_2$ are considered as $C_{3+}$ in this example and the product is the reaction product yield from the converted pyrolysis feed. In diagram 130, certain values for a $C_2U$ yield 135 in wt % of the product, ethylene to acetylene weight ratio 136, and $C_{3+}$ to $C_2U$ weight ratio 137 are shown in weight fraction (or weight ratio) along the Y-axis 132 for various pressures (in psig) along the X-axis 134. The ethylene to acetylene weight ratio 136 and $C_{3+}$ to $C_2U$ weight ratio 137 increases with increasing pressure, while the $C_2U$ yield 135 decreases slightly with increasing pressure. Similarly, in diagram 140, certain values for a $C_2U$ yield 145 in wt % of the product, ethylene to acetylene weight ratio 146, and $C_{3+}$ to $C_2U$ weight ratio 147 are shown in weight fraction (or weight ratio) along the Y-axis 142 for various pressures (in psig) along the X-axis 144. The ethylene to acetylene weight ratio 146 increases with increasing pressure, while the $C_2U$ yield 145 and $C_{3+}$ to $C_2U$ weight ratio 147 are relatively constant with increasing pressure. As such, operating conditions of the thermal pyrolysis reactor may be adjusted to enhance the acetylene yield for a pyrolysis feed.

Further, as it may be appreciated, different types of thermal pyrolysis reactors may have different heat profiles. That is, some embodiments of thermal pyrolysis reactors may operate in an isothermal manner with the heat profile being relatively constant, as noted above. However, other thermal pyrolysis reactors may have a heat profile that is similar to a Gaussian curve. For example, a regenerative reactor may be characterized by an initial and final temperature of 300° C. and a peak pyrolysis gas temperature of 1700° C. for a residence time of 35 ms (≤10 ms at temperature ≥1000° C.), the pressure effect on selectivity is even more dramatic as shown in Table 3 below.

The variations of pressure at high-severity operating conditions for a regenerative reactor are described below in Table 3 and FIGS. 1E and 1F. Table 3 includes simulation results for different ratios of reactor products produced at different pressures for different temperatures from a methane feed. Pyrolysis, in this example, is carried out under regenerative conditions resulting in a Gaussian-like temperature profile with inlet and outlet around 300° C. and with peak temperature of 1704° C. in one set of simulations and of 1783° C. in the other. About 25% of the residence time of the regenerative pyrolysis profile is at temperature above 1200° C. The pyrolysis of this example is carried out with 2:1 molar diluent of hydrogen in a methane feed, and at various reactor pressures between 3 psig (21 kPag) and 162 psig (1117 kPag). All products larger than $C_2$ are considered as $C_{3+}$ in this example and the product is the reaction product yield from the converted pyrolysis feed.

TABLE 3

70% Regenerative Conversion Data

| Peak Temp (° C.) | Pres. (psig) | time (sec) | Conv. | Products (weight percent) | | | | | $C_2U$ | $C_{3+}/C_2U$ | E/A |
|---|---|---|---|---|---|---|---|---|---|---|---|
| | | | | $H_2$ | $CH_4$ | $C_2H_2$ | $C_2H_4$ | $C_{3+}$ | | | |
| 1704 | 3 | 0.034 | 70% | 30.4 | 24.3 | 34.3 | 3.0 | 7.9 | 37.3 | 0.21 | 0.09 |
| 1704 | 15 | 0.034 | 72% | 30.7 | 22.2 | 33.6 | 5.0 | 8.4 | 38.6 | 0.22 | 0.15 |
| 1704 | 29 | 0.034 | 74% | 30.7 | 21.2 | 31.6 | 7.4 | 8.8 | 39.0 | 0.23 | 0.24 |
| 1704 | 36 | 0.034 | 74% | 30.6 | 21.0 | 30.5 | 8.5 | 8.9 | 39.0 | 0.23 | 0.28 |
| 1704 | 59 | 0.034 | 74% | 30.3 | 21.1 | 26.8 | 11.6 | 9.2 | 38.4 | 0.24 | 0.43 |
| 1704 | 103 | 0.034 | 71% | 29.4 | 23.1 | 20.1 | 15.6 | 9.1 | 35.7 | 0.26 | 0.78 |
| 1704 | 162 | 0.034 | 66% | 28.1 | 27.5 | 13.5 | 17.2 | 8.6 | 30.7 | 0.28 | 1.27 |
| 1783 | 15 | 0.011 | 67% | 30.0 | 26.5 | 33.4 | 3.0 | 7.1 | 36.3 | 0.20 | 0.09 |
| 1783 | 36 | 0.011 | 69% | 30.2 | 24.5 | 32.5 | 5.0 | 7.6 | 37.5 | 0.20 | 0.15 |
| 1783 | 44 | 0.011 | 70% | 30.2 | 24.2 | 31.9 | 5.8 | 7.8 | 37.6 | 0.21 | 0.18 |
| 1783 | 74 | 0.011 | 70% | 30.1 | 23.7 | 29.4 | 8.3 | 8.0 | 37.7 | 0.21 | 0.28 |
| 1783 | 103 | 0.011 | 70% | 29.8 | 23.8 | 26.7 | 10.6 | 8.1 | 37.3 | 0.22 | 0.40 |
| 1783 | 162 | 0.011 | 69% | 29.2 | 25.0 | 21.8 | 13.9 | 8.1 | 35.6 | 0.23 | 0.64 |

As shown in Table 3, as pressure increases from 3 psig (21 kPag) to 162 psig (1117 kPag), $C_2U$ yields decrease at a slow rate from 37 wt % to 31 wt % for a 33 ms residence time in a temperature profile that peaks at 1704° C. However, the E/A weight ratios increase rapidly with the increase in pressure. For the profile having peak temperature of 1784° C. and an 11 ms residence time, the $C_2U$ yields are roughly constant at about 37 wt %, while the E/A weight ratio again increases with increasing pressure. Accordingly, the higher pressures tend to lead to higher E/A weight ratios, while the $C_{3+}$ levels at these different temperatures and pressures remain relatively constant at around 8 wt % for the two profiles. As a result, the $C_{3+}$ to $C_2U$ weight ratio increases at slow rate for these different temperatures with the higher temperature providing roughly constant $C_{3+}$ to $C_2U$ weight ratio, but the E/A weight ratio increases at a larger rate. Moreover, higher pressures do not have a significant impact on $C_{3+}$ levels as the $C_{2+}$ to $C_2U$ weight ratio remains almost constant, which is an enhancement over the isothermal reactors.

From this table, the regenerative reactor may be utilized to further optimize the distribution the yield of $C_2U$ (e.g., acetylene yield relative to the ethylene yield) for certain operating conditions. That is, a specific pressure, temperature and residence time may be utilized to optimize the distribution of $C_2U$ yield along with the heat profile of the reactor. These operating conditions may be characterized by the $C_{3+}$ to $C_2U$ weight ratio along with an E/A weight ratio, which may be further explained in view of the FIGS. 1E and 1F.

Figure 1E:
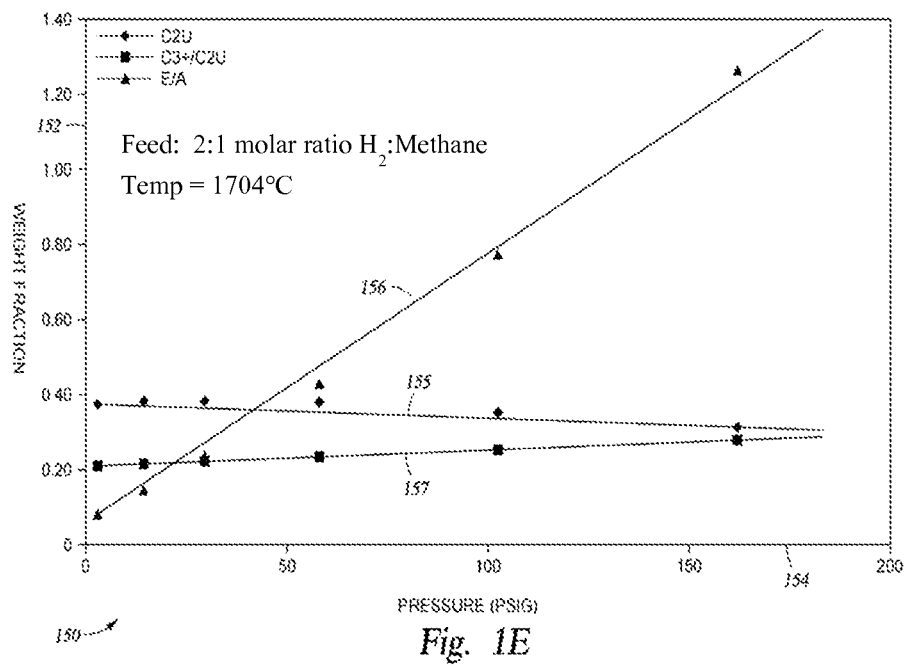
Figure 1F:
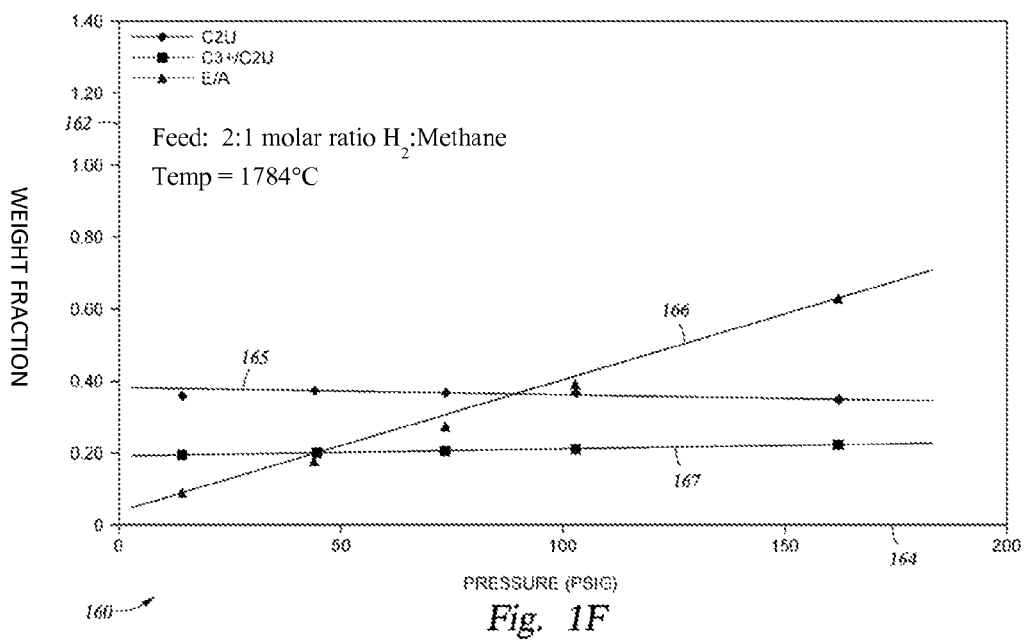

FIGS. 1E and 1F illustrate that the simulation results for different ratios of reactor products produced at different pressures for certain temperatures from a methane feed. The results of operating at the various pressures are provided for comparison of the product yields achievable at the residence times associated with the $C_2U$ yield and E/A weight ratio for that pressure. Pyrolysis, in this example, is carried out under regenerative reactor thermal conditions, with 2:1 molar diluent of hydrogen in a methane feed, and with a peak temperature of 1704° C. for diagram 150 and of 1784° C. for diagram 160. All products larger than $C_2$ are considered as $C_{3+}$ in this example and the product is the reaction product yield from the converted pyrolysis feed. In diagram 150, certain values for $C_2U$ yield 155 in wt % of the product, ethylene to acetylene weight ratio 156, and $C_{3+}$ to $C_2U$ weight ratio 157 are shown in weight fraction (or weight ratio) along the Y-axis 152 for various pressures (in psig) along the X-axis 154. The ethylene to acetylene weight ratio 156 and $C_{3+}^+$ to $C_2U$ weight ratio 157 increases with increasing pressure, while the $C_2U$ yield 155 decreases slightly with increasing pressure. Similarly, in diagram 160, certain values for $C_2U$ yield 165 in wt % of the product, ethylene to acetylene weight ratio 166, and $C_{3+}$ to $C_2U$ weight ratio 167 are shown in weight fraction (or weight ratio) along the Y-axis 162 for various pressures (in psig) along the X-axis 164. The ethylene to acetylene weight ratio 166 increases with increasing pressure, while the $C_2U$ yield 165 and $C_{3+}$ to $C_2U$ weight ratio 157 are relatively constant with increasing pressure. As such, operating conditions of the regenerative thermal pyrolysis reactor may be adjusted to enhance the distribution of the ethylene yield and/or acetylene yield for a pyrolysis feed.

Although the E/A weight ratio continues to improve with increasing pressure, certain limiting factors may hinder higher pressure operations. For instance, eventually high pressure operating conditions may lead to unacceptable $C_{3+}$ to $C_2U$ weight ratios and/or lower $C_2U$ yields. Further, equipment utilized in the system may be limited to certain pressure ranges. Accordingly, preferred operating pressures may include pressures ≥36 psig (248 kPag), or ≥44 psig (303 kPag) or ≥103 psig (710 kPag), but may be ≤300 psig (2068 kPag), or ≤163 psig (1124 kPag), or ≤150 psig (1034 kPag). As may be appreciated, these different pressures may be combined together to form different combinations depending on the specific configuration of equipment.

In addition, it is beneficial to maintain longer residence times and lower temperatures to maximize E/A weight ratio. However, such residence times and temperatures result in higher weight ratios of $C_{3+}$ to $C_2U$. Accordingly, the design and operating conditions may be adjusted to provide a balance between the E/A weight ratio and the $C_{3+}$ to CU weight ratio. That is, the thermal pyrolysis reactor may be operated at lower temperatures to maximize the E/A weight ratio at an efficient and operable $C_{3+}$ to $C_2U$ weight ratio. For instance, the operation of the pyrolysis unit and hence operating conditions may be optimized based on objectives for the pyrolysis unit performance. As an example, the operating conditions, such as the peak pyrolysis gas temperatures and/or pressure, of the thermal pyrolysis reactor may be adjusted based on an optimized value from an optimization function that comprises an ethylene to acetylene weight ratio and the $C_{3+}$ to $C_2$ unsaturate weight ratio. In another example, when the objective is a high E/A weight ratio, the pyrolysis reactor may be optimized by (i) using a regenerative reactor or other reactor having Gaussian-like temperature profile, (ii) increasing design operating temperature to be above a minimum level needed to achieve an acceptably low value of $C_{3+}/C_2U$ (which may be referred to as a coke operability limit), and then (iii) increasing design operating pressure as much as possible given other reactor and system constraints. In another example, if the objective is a product with a minimal E/A weight ratio, the reactor may be optimized by (i) using a reactor that gives a isothermal temperature profile, (ii) operating the reactor at the lower end of the preferred pressure range, such as from about 36 psig (248 kPag) to about 59 psig (407 kPag), and (iii) increasing temperature as much as possible within the reactor materials constraints.

The thermal pyrolysis reactor may be limited to certain pressures by various limitations. For instance, at higher pressures and constant residence times, mass density of the gas increases and thus requires higher heat transfer rates per unit of reactor volumes. This heat transfer rate may exceed the capability of the reactor internals or may lead to exceedingly small channels or exceedingly large numbers of channels per square inch (CPSI). Thus, these limitations may eventually lead to impractical reactor dimensions and impractically high levels of pressure drop.

Unless otherwise stated, all percentages, parts, ratios, etc., are by weight. Unless otherwise stated, a reference to a compound or component includes the compound or component by itself, as well as in combination with other compounds or components, such as mixtures of compounds. Unless otherwise stated, all pressures are given as gauge pressure, which is as pressures above standard atmospheric pressure (e.g., psig).

Further, when an amount, concentration, or other value or parameter is given as a list of upper preferable values and lower preferable values, this is to be understood as specifically disclosing all ranges formed from any pair of an upper preferred value and a lower preferred value, regardless whether ranges are separately disclosed.

The terms "convert" and "converting" are defined broadly herein to include any molecular decomposition, cracking, breaking apart, conversion, and/or reformation of organic molecules (hydrocarbons) in the feed, by means of at least pyrolysis heat, and may optionally include supplementation by one or more of catalysis, hydrogenation, diluents, and/or stripping agents.

As used herein, the expression "non-volatiles" may be defined broadly herein to mean substantially any resid, metal, mineral, ash, ash-forming, asphaltenic, tar, coke, and/or other component or contaminant within the feedstock that does not vaporize below a selected boiling point or temperature and which, during or after pyrolysis, may leave an undesirable residue or ash within the reactor system, which is difficult to remove. Noncombustible nonvolatiles may include ash, for example. Methods for determining asphaltenes and/or ash may include American Society of Testing and Materials (ASTM) methods, such as methods for asphaltenes may include ASTM D-6560 and D-7061 and methods for ash may include ASTM D-189, D-482, D-524, and D-2415.

As used herein, the terms "coke" and "soot" may refer to hydrocarbonaceous material that accumulates within the reactor during pyrolysis or to solid-phase hydrocarbonaceous materials that emerge from the reactor with pyrolysis effluent. The hydrocarbonaceous material that accumulates within the reactor during pyrolysis may also be defined as the fraction of the pyrolysis feed that remains in a thermal pyrolysis reactor and thus does not emerge from the reactor as pyrolysis effluent. Coke and soot are components of the reactor product, which are included for $C_{3+}$ product for pyrolysis selectivity. The terms "$C_3^+$" and "$C_{3+}$" mean all products of the pyrolysis feed having more than three carbon atoms, which include coke and soot, whether those products emerge from the reactor or remain within the reactor. The reactor product that does emerge may be referred to as the reactor effluent, which is at least a portion of the reactor product.

The term "pyrolysis feed" means the composition, which may be a mixture, subjected to pyrolysis. In one embodiment, the pyrolysis feed is derived from a hydrocarbon feed (e.g., by separation of a portion from the hydrocarbon feed and optional addition of diluents).

As used herein, the "hydrocarbon feed" contains hydrocarbons (C bound to H) and may contain (i) minor components of heteroatoms (<10 wt %) covalently bound to hydrocarbons and (ii) minor components of heteroatoms (<10 wt %) not bound to hydrocarbons (e.g., $H_2O$), wherein these weight percents are based on the weight of the hydrocarbon feed. The term "hydrocarbons in the hydrocarbon feed" or "hydrocarbons of the hydrocarbon feed" means molecules within the hydrocarbon feed that contain at least hydrogen and carbon and, optionally, heteroatoms covalently bound to a portion of such molecules. Weight percents of hydrogen and carbon, as used to characterize the hydrocarbon feed, are provided as a percent of the hydrocarbons in the hydrocarbon feed. The hydrocarbon feed may include, by way of non-limiting examples, one or more of Fischer-Tropsch gases, methane, methane containing streams such as coal bed methane, biogas, associated gas, natural gas and mixtures or components thereof, steam cracked gas oil and residues, gas oils, heating oil, jet fuel, diesel, kerosene, gasoline, coker naphtha, steam cracked naphtha, catalytically cracked naphtha, hydrocrackate, reformate, raffinate reformate, Fischer-Tropsch liquids, natural gasoline, distillate, virgin naphtha, crude oil, atmospheric pipestill bottoms, vacuum pipestill streams including bottoms, wide boiling range naphtha to gas oil condensates, heavy non-virgin hydrocarbon streams from refineries, vacuum gas oils, heavy gas oil, naphtha contaminated with crude, synthetic crudes, shale oils, coal liquefaction products, coal tars, tars, atmospheric resid, heavy residuum, C4's/residue admixture, naphtha residue admixture, cracked feedstock, coker distillate streams, hydrocarbon streams derived from plant or animal matter, and/or any mixtures thereof.

As used herein, the expression "advantaged feed" means a feed that has a lower cost (per ton or per heating value) than Brent reference crude oil and may include, by way of non-limiting examples, one or more methane containing feeds and one or more high-aromatic containing streams. Some examples may include one or more of Fischer-Tropsch gases, methane, methane containing streams such as coal bed methane, biogas, associated gas, natural gas and mixtures or components thereof, steam cracked gas oil and residues, gas oils, coker naphtha, steam cracked naphtha, catalytically cracked naphtha, hydrocrackate, reformate, raffinate reformate, natural gasoline, Fischer-Tropsch liquids, virgin naphtha, crude oil, atmospheric pipestill bottoms, vacuum pipestill streams including bottoms, wide boiling range naphtha to gas oil condensates, heavy non-virgin hydrocarbon streams from refineries, vacuum gas oils, heavy gas oil, naphtha contaminated with crude, synthetic crudes, shale oils, coal liquefaction products, coal tars, tars, atmospheric resid, heavy residuum, C4's/residue admixture, naphtha residue admixture, cracked feedstock, coker distillate streams, and/or any mixtures thereof.

The term "hydrogen content" means atomic hydrogen bound to carbon and/or heteroatoms covalently bound thereto and which excludes molecular hydrogen ($H_2$) in the hydrocarbon feed expressed as a weight percent based on the weight of the hydrocarbons in the hydrocarbon feed. Hydrogen content as applied to pyrolysis feed or reactor feed are expressed as a weight percent of hydrocarbons in the respective feed. A hydrocarbon feed may have a hydrogen content in the range of 6 wt % (weight percent) to 25 wt %, 8 wt % to 20 wt % (e.g., not natural gas), or 20 wt % to 25 wt % (e.g., natural gas). The hydrocarbon feed may be provided directly as the pyrolysis feed, may optionally be mixed with one or more diluent feeds to form the pyrolysis feed, or may have a portion of the hydrocarbon feed removed (e.g., removal of nonvolatiles at the operating conditions of the reactor) to form the pyrolysis feed. That is, the pyrolysis feed may be derived from the hydrocarbon feed. The pyrolysis feed may include hydrogen gas ($H_2$) in an amount that provides a preferred ratio of hydrogen gas ($H_2$) moles to the total moles of carbon (C) in the hydrocarbon components of the pyrolysis feed. The ratio of hydrogen to carbon ($H_2/C$) in the pyrolysis feed may be from 0.0 or 0.1 to 5.0, such as 0.0, 0.1, 1.0, 2.0, 3.0, 4.0, 5.0, or values in between. Combining the hydrogen content of the hydrogen gas to the hydrogen and carbon contents of the hydrocarbon components of the pyrolysis feed may result in a weight percent of total hydrogen in the pyrolysis feed that is greater than that in the hydrocarbon feed. For example, the weight percent of total hydrogen in the pyrolysis feed may be between 8 wt % and 54 wt %.

As used herein, the expression "combustion feed" means the two or more individual feeds that are to be combined to form a combustion reaction or a mixture of two or more feeds, such as a combustion fuel that does not contain oxidants (e.g., $O_2$) or non-combustible non-volatiles and a combustion oxidant that may include an oxygen or oxygen containing fluid. The combustion fuel may include, by way of non-limiting examples, one or more of Fischer-Tropsch gases, methane, methane containing streams such as coal bed methane, biogas, associated gas, natural gas and mixtures or components thereof, synthesis gas (mixtures of CO and $H_2$) and hydrogen. The combustion oxidant may include, but are not limited to, air, oxygen or mixtures thereof. Any of the combustion feed, fuel, or oxidant may additionally include non-combustible but volatile diluents such as $N_2$, $CO_2$, $H_2O$, and/or other inert gases.

The term "reactor", as used herein, refers to equipment used for chemical conversion. As such, several items identified as reactors may be combined to become a single entity that is also identified as a reactor, in that individual and combined entities may all be characterized as equipment used for chemical conversion. The regenerative reverse-flow thermal pyrolysis reactors described herein may comprise first and second reactor entities, for example as described in U.S. Patent Application Publication No. 2007/0191664.

The term "pyrolysis reactor", as used herein, refers to a system for converting hydrocarbons by means of at least pyrolysis chemistry. The pyrolysis reactor may include one or more reactors and/or associated equipment and lines. A region, as used herein, refers to a location within the pyrolysis reactor, which may include one or more reactors and/or associated equipment and lines. The region may include a specific volume within a reactor, a specific volume between two reactors and/or the combination of different disjointed volumes in one or more reactors. The regenerative reverse-flow thermal pyrolysis reactors described herein may comprise first pyrolysis reactor and second pyrolysis reactor, for example as described in U.S. Patent Application Publication No. 2007/0191664.

As used herein, the "thermal pyrolysis reactor" includes at least predominantly pyrolysis chemistry. Pyrolysis or pyrolysis chemistry, such as the conversion of hydrocarbons to unsaturates such as ethylene and acetylene, is an endothermic process requiring addition of heat. The terms crack and cracking may be used interchangeably with the terms pyrolyze and pyrolysis. In a thermal pyrolysis reaction, ≥50%, ≥80%, or ≥90%, of this heat is provided by heat transfer via solid surfaces such as tubulars or bed materials. Any combustion chemistry that occurs within the pyrolysis stream of a thermal pyrolysis reactor provides a minority of the endothermic heat of pyrolysis, such as <50%, <20%, or <10% of the endothermic heat of pyrolysis.

The term "high-severity operating conditions" means pyrolysis conditions resulting in the conversion of the a pyrolysis feed comprising hydrocarbons to make a product having an acetylene content≥10.0 wt % based on the weight of the hydrocarbons in the pyrolysis feed. The operating conditions for a thermal pyrolysis reactor may be characterized by a severity threshold temperature that divides low-severity operating conditions in thermal pyrolysis reactors from high-severity operating conditions in thermal pyrolysis reactors. The severity threshold temperature is defined as the lowest temperature at which the feed to the reactor may react at a residence time≤0.1 sec (second) to make at least 10 wt % acetylene as a percent of the hydrocarbons in the feed evaluated at the given operating conditions of the process. The high-severity operating conditions for a thermal pyrolysis reactor may be characterized as peak pyrolysis gas temperatures that are greater than the severity threshold temperature. The low-severity thermal pyrolysis reactor may be characterized as pyrolysis gas temperatures that are less than the severity threshold temperature and no pyrolysis gas temperatures that exceed the severity threshold temperature. For example, for the thermal conversion of methane at a pressure of 14.7 psig (101 kPag) and with 2:1 molar ratio of hydrogen diluent, the threshold temperature is about 1274° C. for this process. At temperatures at or above 1274° C., yields of acetylene can exceed 10 wt % of the starting methane, at some time≤0.1 seconds. Conversely, at temperatures below 1274° C., there are no times≤0.1 seconds for which yields of acetylene reaches 10 wt % of the starting methane.

According to one or more embodiments of the present techniques, an enhanced process is provided for the production of $C_2U$ (e.g., acetylene and ethylene), which are useful for manufacturing polyolefins and other petrochemical products. The process may include various stages, such as feed preparation, pyrolysis, recovery and further processing, such as separation of the polymer grade monomer and polymerization to polyethylene. The thermal pyrolysis reactor may have operating conditions that are below a specific selectivity threshold, such as a $C_{3+}$ to acetylene weight ratio ≤0.5, or ≤0.45 or ≤0.4. Operation at low levels of $C_{3+}$ to acetylene is desirable both to improve process economics and to improve process operability. Economics are improved by low $C_{3+}$ to acetylene weight ratio because $C_{3+}$ products produced by high-severity pyrolysis are less valuable than the acetylene product. Further, operability is improved by low $C_{3+}$ to acetylene weight ratio because $C_{3+}$ products may include substantial amounts of coke, whose production may hinder operations. Specifically, coke produced in excess amounts may result in an inability to maintain the thermal pyrolysis reactor channels available for fluid flow, and coke produced in excess amounts may result in heat release (during combustion and/or regeneration steps), which is greater than the heat amounts that may be used in the process or reactor. At least a portion of the reactor product may be further processed to recover polyethylene, polyolefins, benzene or other products.

Further, in one or more embodiments of the present techniques, an enhanced process is provided for the production of a specific distribution of $C_2U$ (e.g., acetylene yield and ethylene yield), which are useful for manufacturing polyolefins and other petrochemical products. In particular, the present techniques may involve operating conditions that may result in a $C_{3+}$ to $C_2U$ weight ratio ≤0.5, or ≤0.4, or ≤0.3, while the ethylene to acetylene weight ratio is ≥0.08, or ≥0.1, or ≥0.2 or ≥0.5. These operating conditions may be utilized to manage the amount of ethylene and acetylene for further processing. By managing the size and capacity of the equipment for acetylene conversion, the process units may be smaller and involve less capital expense. Further, by operating at certain pressure ranges, the use of compression for recovery stages may be minimized or eliminated.

Accordingly, the present techniques may involve operating the thermal pyrolysis reactor at different operating conditions. These operating conditions may include adjusting operational settings to adjust the pressure within the reactor and/or the temperature within a reactor. The operational settings may include increasing the heat generated by providing different combustion feeds to the thermal pyrolysis reactor. The present techniques may be further understood with reference to FIGS. 2 to 4, which are discussed below.

Figure 2:
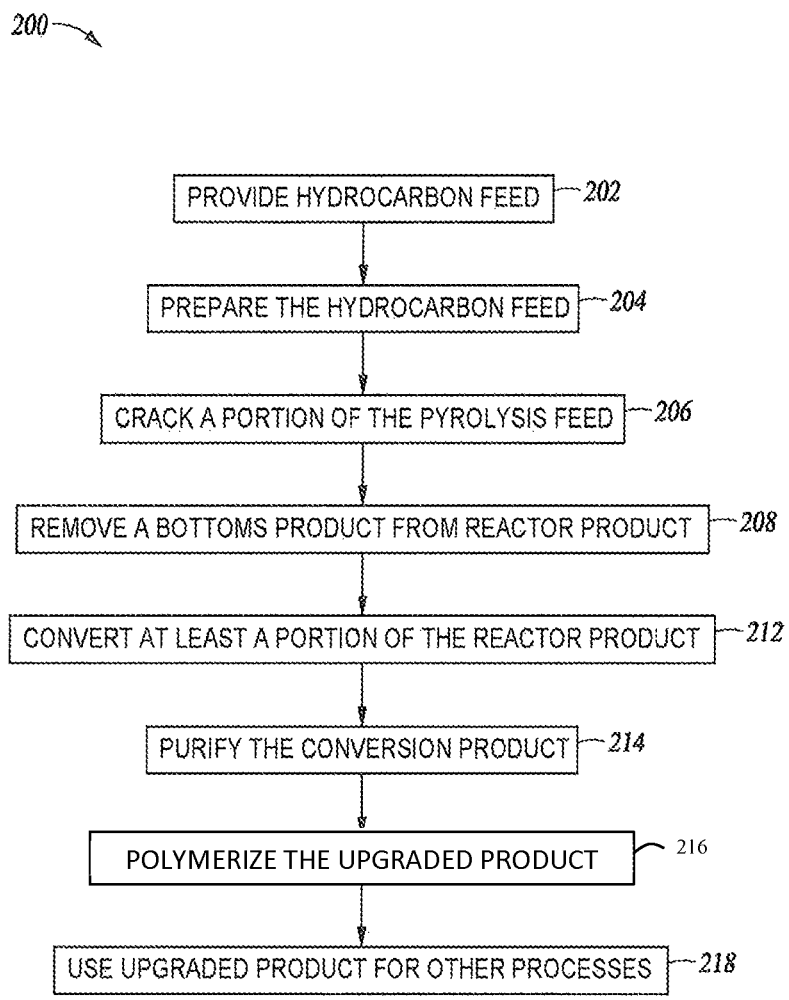
FIG. 2 is a simplified process flow diagram illustrating an embodiment of the present techniques.

To begin, an exemplary embodiment of the present techniques is illustrated in the block flow diagram 200 of FIG. 2. In this flow diagram 200, a process for the production of olefins, such as ethylene, which may subsequently be used in the manufacture of polyolefins, such as polyethylene, is shown. In this block diagram, the process includes various stages. For instance, a feed preparation stage is described in block 204. A cracking stage is described in block 206, which involves cracking the pyrolysis feed in a thermal pyrolysis reactor to produce a reactor product. The pyrolysis reactor may be utilized at high-severity operating conditions that manage the $C_{3+}$ to $C_2U$ weight ratio ≤0.5, or ≤0.4, or ≤0.3, while the ethylene to acetylene weight ratio is ≥0.08, or ≥0.1, or ≥0.2 or ≥0.5. Further, the reactor may be operated at operating conditions that produces a reactor product that has $C_{3+}$ to acetylene weight ratio of ≤0.5, or ≤0.45, or ≤0.4. The CU components (e.g., acetylene and ethylene) of the reactor product may represent ≥20 wt %, ≥50 wt %, or ≥80 wt %, or ≥90 wt % of the total $C_{2+}$ gas phase components of the reactor product. Then, a recovery stage is described in blocks 208 to 214, which further processes the reactor product or reactor effluent to recover a conversion product, such as ethylene and/or propylene. Finally, a polymerization stage may be performed, as described in block 216, allowing the polymerized product to be used for other processes, described in block 218.

At block 202, a hydrocarbon feed is provided. As noted above, the hydrocarbon feed may include one or more of methane, natural gas, petroleum or petrochemical liquids and mixtures thereof, or other suitable hydrocarbon feeds, as noted above. At block 204, the hydrocarbon feed may be subjected to various feed preparation processes to form the pyrolysis feed or may be provided directly to the thermal pyrolysis reactor as the pyrolysis feed. That is, the pyrolysis feed may be derived from the hydrocarbon feed. For example, the feed preparation processes optionally include removal of impurities or contaminants prior to cracking. The feed preparation process may include mixing the hydrocarbon feed with a diluent feed. The feed preparation processes may include one or more of condensate and water removal units, acid gas removal units (e.g., caustic or amine treater units), dehydration units (e.g., glycol units), nitrogen removal units, hydrogenation, demetalation, visbreaking, coking and/or vapor/liquid separators. The impurities or contaminants, which may include one or more of carbon dioxide, carbon monoxide, sulfur species, oxygenates and non volatiles (e.g., metal), may be conducted away from the process. In a preferred embodiment, the hydrocarbon feed may include non-volatiles, which are materials that are not in the gas phase (i.e. are components that are in the liquid or solid phase) at the temperature, pressure and composition conditions of the inlet to the pyrolysis reactor. Non-combustible non-volatiles (e.g., ash; ASTM D-189) are preferably limited to ≤2 parts per million weight (ppmw) on hydrocarbon feed, more preferably ≤1 ppmw. Combustible non-volatiles (e.g., tar, asphaltenes, ASTM D-6560) may be present at concentrations below 5% of the hydrocarbon feed, preferably at concentrations below 1%, more preferably at concentrations below 100 ppmw, and most preferably at concentrations below 10 ppmw of the total hydrocarbon feed to the pyrolysis reactor, as long as the presence of the combustible non-volatiles do not result in excessive (e.g., ≥2 or ≥1 ppmw) concentrations of non-combustible non-volatiles. As a first example, the hydrocarbon feed may comprise crude oil and crude oil components. As a second example, the pyrolysis feed may comprise substantially methane (e.g., ≥50 wt %, ≥75 wt %, or ≥90 wt % of the pyrolysis feed).

After the feed preparation stage, the pyrolysis feed is cracked in block 206. The cracking of the pyrolysis feed may involve the use of a thermal pyrolysis reactor to convert the pyrolysis feed into a reactor product. The reactor product includes one or more $C_2U$, and optionally includes hydrogen ($H_2$), methane, ethane, methyl acetylene, diacetylene, and $C_{3+}$ products (e.g., benzene, tars, soot, etc.). The reactor product includes components that emerge from the reactor and those that remain within the reactor, if any, as a result of pyrolysis (e.g., coke may remain in the reactor and later emerge as a portion of the combustion products). The amount of coke remaining in the reactor may be determined from a mass balance of the process. Further, the thermal pyrolysis reactor may include any of a variety of thermal pyrolysis reactors, such as a regenerative reverse flow reactor, as described in U.S. Patent Application Publication No. 2007/0191664. Other embodiments may include a thermal pyrolysis reactor, as described in U.S. Pat. No. 7,491,250, U.S. Patent Application Ser. No. 61/349,464 and U.S. Patent Application Publication Nos. 2007/0144940, 2007/0191664 and 2008/0142409. Regardless of the specific type of thermal pyrolysis reactor, it may operate at peak pyrolysis gas temperatures between 1200.0° C. and 2200.0° C., preferably between 1400.0° C. to 1900.0° C. In particular, for reactors with an isothermal heat profile, the temperatures may be between 1450.0° C. and 1700.0° C., or between 1540.0° C. and 1650.0° C. For reactors with a Gaussian like heat profile, the peak pyrolysis gas temperatures may be between 1540.0° C. and 2200.0° C. or between 1600.0° C. and 1800.0° C. In addition, the process may involve pressures ≥36 psig (248 kPag), or ≥44 psig (303 kPag) or ≥103 psig (710 kPag), but may be ≤300 psig (2068 kPag), or ≤163 psig (1124 kPag), or ≤150 psig (1034 kPag). For a regenerative reverse flow reactor, it may be operated to have a cycle time of the combustion step and the pyrolysis step that is between 0.5 second to 30 seconds. Further, for a regenerative reverse flow reactor, the pressure in the pyrolysis step may be similar or different to the pressure in the combustion step (e.g., at lower or higher pressure than the pyrolysis step).

At least a portion of the reactor product may be conducted away for storage or further processing. Optionally, one or more upgrading processes may be included in the recovery stage, as shown in blocks 208 to 214. At block 208, the reactor product from the reactor may be subject to a separation process to provide a bottoms product. The separation may remove one or more bottom products comprising solids, such as higher boiling point materials (e.g., contaminates, solids or impurities) from the $C_2U$ in reactor product. The separation process may include a tar and/or solid removal process, compression, adsorption, distillation, washing, and drying of the remaining reactor product, and/or any combination of one or more of these processes.

At block 212, the remaining reactor product may optionally be provided to an acetylene conversion process. The remaining reactor product may be in liquid phase, vapor phase or a mixture thereof, and may be subjected to an acetylene conversion process that is performed by a catalyst in the liquid phase, vapor phase or a mixture thereof. For instance, the acetylene conversion process may include acetylene hydrogenation in an isothermal, slurry or adiabatic catalytic reactor, or other suitable conventional techniques. The catalytic reactor may employ group VI or VIII catalyst, catalyst bimetal or trimetal blends on an alumina, silica or other support, as is well known in the art. For example, the acetylene in the reactor product is absorbed into a liquid, hydrogenated within that liquid and then the ethylene product is desorbed from the liquid. At block 214, conversion products, which include ethylene, may optionally be provided to a purification process. The purification process may include (multistage) distillation or refrigerated distillation including a demethanator tower and $C_2$ splitter.

Should additional upgrading or purification of the conversion products be desired, purification systems, such as that found in *Kirk-Othmer Encyclopedia of Chemical Technology*, 4th edition, Volume 9, John Wiley & Sons, 1996, pg. 894-899, may be used. In addition, purification systems, such as that described in *Kirk-Othmer Encyclopedia of Chemical Technology*, 4th edition, Volume 20, John Wiley & Sons, 1996, pg. 249-271, may also be used. Other examples may be found in U.S. Pat. Nos. 6,121,503; 5,960,643; 5,364,915; 5,238,892; 5,280,074; 5,288,473; 5,102,841; 4,956,426; 4,508,842; and EP Patent No. 0612753; and EP Patent No. 0012147.

Optionally, the upgraded product is conducted away for storage or for further processing, such as conversion into polyethylene. At block 216, the polymerization may include both the gas phase and solution polymerization methods, which conventional processes and may be employed in the practice of the present techniques. As an example, U.S. Pat. Nos. 6,822,057; 7,045,583; 7,354,979 and 7,728,084 describe different ethylene polymerization processes that may be utilized.

Optionally, the conversion product (e.g., ethylene) may be provided for other processes or used commercially as a final product. These processes may include generating ethylene glycol or other products. As an example, the ethylene stream may be treated, separated and polymerized to form plastic compositions, which may include polyolefins, particularly polyethylene. Any conventional process for forming polyethylene may be used, while catalytic processes are preferred. Particularly preferred are metallocene, Ziegler/Natta, aluminum oxide and acid catalytic systems. Examples may include U.S. Pat. Nos. 3,258,455; 3,305,538; 3,364,190; 5,892,079; 4,659,685; 4,076,698; 3,645,992; 4,302,565; and 4,243,691. In general, these methods involve contacting the ethylene product with a polyolefin-forming catalyst at a pressure and temperature effective to form the polyolefin product.

Beneficially, the proposed process provides various enhancements over previous techniques. For instance, the process provides flexibility in managing byproducts or contaminants. That is, the process may be operated in a manner that does not involve additional stages to remove various contaminants, which improves the efficiency of the process. As an example, typical high-severity pyrolysis processes, such as partial combustion, typically utilize oxygen in the reaction with the pyrolysis feed, which produces carbon monoxide and carbon dioxide in the reactor product. By not utilizing an oxygen containing stream in the pyrolysis stage of the present techniques, various impurities, such as CO and $CO_2$, are not inherently present in the reactor product, which reduces the cost and difficulties in managing these impurities through the process.

Also, the process may manage impurities based on the operating conditions of the thermal pyrolysis reactor. That is, the present techniques expose the pyrolysis feed to specific operating conditions that may be used to manage the production of coke and other impurities. These operating conditions may include peak pyrolysis gas temperatures ≥1540° C. or other suitable operating conditions. These operating conditions may comprise a peak pyrolysis gas temperature equal to or above 1400° C. and a $C_{3+}$ to acetylene weight ratio ≤0.5, ≤0.45 and ≤0.4, as noted above. These operating conditions may be adjusted to manage $C_{3+}$ production in the reactor process. As an example, certain impurities in the feed (e.g., asphaltenes and/or mercaptans) may be provided to the reactor and converted into acetylene, ethylene and/or coke. By exposing the feed to these operating conditions, the $C_{3+}$ product, which may include coke, tar and/or coke precursors, may be burned off within the reactor and removed from the process. As a result, feeds with higher asphaltene contents may be managed through the system without the concerns of coking in conventional processes. Other impurities, which may include but are not limited to sulfur and nitrogen containing compounds, oxygenates, mercury (Hg), salts, water, $H_2S$, $CO_2$, and $N_2$, may be removed as different products prior to or after the thermal pyrolysis reactor. That is, unlike other processes, the present techniques utilize operating conditions and the thermal pyrolysis reactor to manage the impurities.

In addition, as noted above, by using high-severity conditions (e.g., higher temperatures) in the pyrolysis stage of the process, the present techniques may enhance $C_2$ selectivity. That is, the pyrolysis stage may crack the pyrolysis feed at residence times that are lower than other processes, such as low-severity processed. As a result, the pyrolysis feed is more efficiently cracked and the reactor size may be smaller (e.g., less capital expense and more efficient).

Further still, using high-severity condition of the thermal pyrolysis reactor provides greater flexibility in the pyrolysis feed utilized in the reactor. That is, the pyrolysis feed may be derived from a broader range of hydrocarbon feeds with lower hydrogen contents and advantaged feeds (e.g., heavy aromatic to methane). These advantaged feeds, which do not typically react in at low-severity operating condition or react to lower value products, react in the process to provide $C_2U$. The high-severity operating conditions, as provided in the present process, converts the aromatic containing and/or methane containing feeds at high levels to valuable $C_2$ products. As such, the process may utilize a broad range of hydrocarbon feeds that foul or are unreactive in other processes.

Moreover, when the thermal pyrolysis reactor is a regenerative reverse flow reactor, the configuration may be used to control the temperature of the reactor product at the reactor outlet to a temperature between 300° C. to 500° C. That is, the process may utilize passive quenching of the process to provide a reactor product that does not have to involve active quenching steps to lower the reactor product temperature.

In addition, for one or more other embodiments of regenerative reverse flow reactors, air may be utilized instead of oxygen gas as part of the combustion process to generate heat for the pyrolysis feed because the combustion step is a separate step from the reaction step. Accordingly, this reactor configuration may reduce capital costs and operational costs by not requiring an oxygen feed (e.g., oxygen purification facilities) and reducing units that are utilized to remove combustion products from the hydrocarbon effluent.

Further, the process may optionally involve other processing steps. For example, between block 208 and 212, the remaining reactor product may be compressed. The compression may include compressors that operate at outlet pressure from 50 psig (345 kPag) to 400 psig (2758 kPag), or more preferably from 150 psig (1034 kPag) to 300 psig (2068 kPag). The use of compressors depends upon the operating pressure of the thermal pyrolysis reactor. Further, the process may involve separation steps that separate at least a portion of the reactor product into an acetylene-rich product or stream and an acetylene-lean product or stream, which may involve separating different products from the remaining reactor product in the recovery stage. The acetylene-rich product may include ≥50 wt % of the acetylene in the reactor product, ≥70 wt % of the acetylene in the reactor product, ≥85 wt % of the acetylene in the reactor product, or even ≥95 wt % of the acetylene in the reactor product. The acetylene-lean product may include from 0 wt % to the remaining portion of the acetylene that is not in the acetylene-rich product. The remaining reactor product may pass through one or more product separation processes, such as a light gas separation or a heavy product separation, to form various products.

For example, after block 208 and prior to block 214, different light gas products (e.g., a portion of the light gas in the reactor product) may be separated as light gas products and the remaining reactor product may form an acetylene-rich product. The light gas removal process may include different separation mechanisms along with a basic wash, for example caustic wash or amine scrubbing, to conduct the light gas products away from the remaining reactor product. For other embodiments, the light gas separation mechanisms may include pressure swing adsorption, membranes, cryogenic distillation, electrochemical separation, liquid absorption and/or liquid phase absorption and light gas desorbtion. The membrane inlet pressure or the pressure swing adsorption inlet pressure may be between 150 psig (1034 kPag) and 250 psig (1724 kPag), while the liquid phase absorption and light gas desorbtion may be performed at pressures between 50 psig (345 kPag) and 250 psig (1724 kPag). The light gas separation mechanisms may be used to separate hydrogen, carbon monoxide, methane, nitrogen and/or other light gases. The light gas products, such as hydrogen and/or methane, separated from the remaining portion of the reactor product may be used as the feed diluent into the thermal pyrolysis reactor, a feed stripping medium, as a fuel for the thermal pyrolysis reactor, or as a byproduct. The light gases may contain a fraction of the methane separated from the remaining reactor product or cracked stock. Further, in some embodiments, the light gas separation may include additional stages or units to remove one or more of carbon dioxide ($CO_2$), hydrogen sulfide ($H_2S$), and water ($H_2O$) but also may include other reactive impurities. In particular, carbon dioxide and hydrogen sulfide, if present, may be removed by washing the stream with a solution of alkali or a salt of an amine or organoamine. If water is present, it may be removed by a methanol treatment, such as described in Belgian Patent No. 722,895. Other methods for removing water are adsorption and extraction by diethylene glycol. Various exemplary embodiments of this process are described further below.

Optionally, after block 208 and prior to block 214, a heavy product separation may conduct away a product of condensables from the remaining reactor product. The condensables may include vaporized liquids that condense, such as benzene, or are separated via cooled separations for example, adsorption, vapor liquid separators, flash drums etc. Certain exemplary embodiments of this process are described further below in FIGS. 3 and 4.

Figure 3:
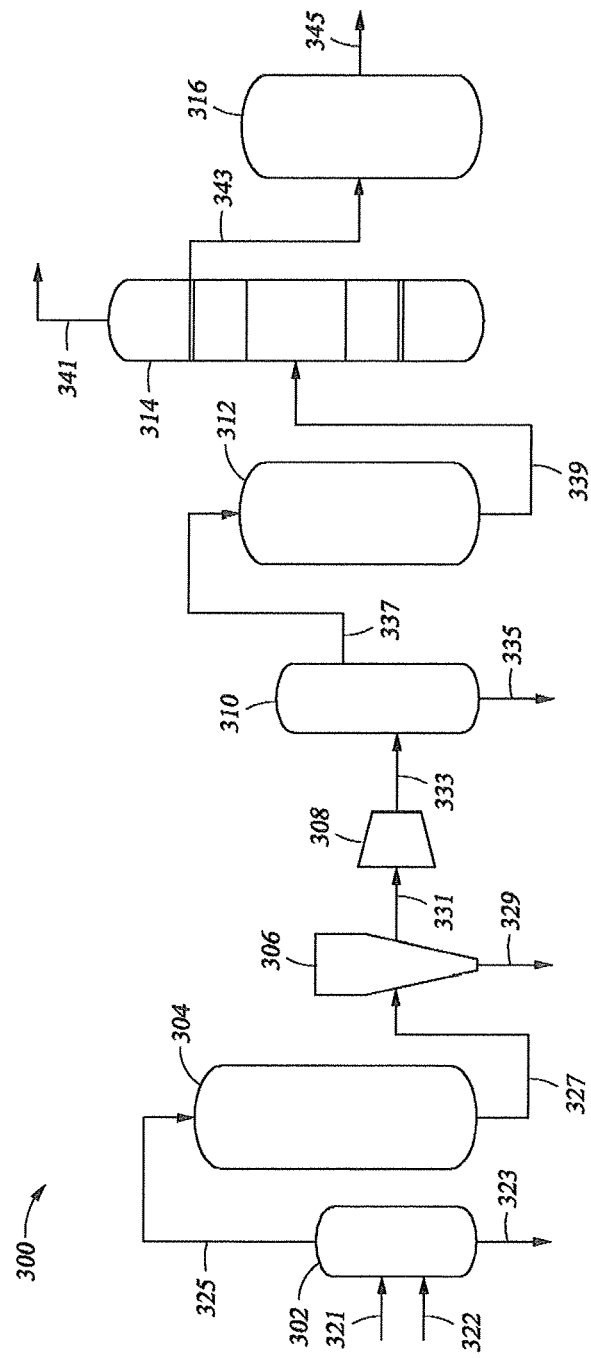
FIG. 3 is a simplified diagrammatic illustration of an exemplary process for converting the hydrocarbon feed to other products in accordance with an embodiment of the present techniques.

FIG. 3 is a simplified diagrammatic illustration 300 of an exemplary process for converting hydrocarbon feed to polyethylene in accordance with an embodiment of the present techniques. In this illustration 300, a particular configuration of unit operations (i.e. units) are coupled together to convert a hydrocarbon feed to polyethylene. These units may include a feed separation unit 302, a thermal pyrolysis reactor 304, solid removal unit 306, a compressor 308, a product separation unit 310, an acetylene converter 312, a purification unit 314 and an ethylene polymerization unit 316. In particular for this configuration, the feed preparation stage may include the feed separation unit 302, the cracking stage may include the thermal pyrolysis reactor 304, the recovery stage may include solid removal unit 306, a compressor 308, a product separation unit 310, an acetylene converter 312, a purification unit 314, and the polyethylene polymerization stage may include the ethylene polymerization unit 316. The process will now be explained in more detail.

A hydrocarbon feed, such as fuel oil (e.g., atmospheric resid) and/or natural gas, or other suitable hydrocarbon feed or blends thereof, is provided via line 321 to the feed separation unit 302. As noted above, the hydrocarbon feed may have a hydrogen content of 6 wt % to 25 wt %, 8 wt % to 20 wt % (e.g., not methane), or 20 wt % to 25 wt % (e.g., natural gas). Optionally, a diluent feed may be provided via line 322, which may include $H_2$, $N_2$, water or a lighter hydrocarbon, which lighter hydrocarbon may be a hydrocarbon with higher hydrogen content relative to the hydrocarbon feed. The diluent feed may be used to adjust the hydrogen content of the hydrocarbon feed to form a pyrolysis feed having a hydrogen content above a certain threshold. Further, the diluent feed or another fluid may be added to adjust the partial pressure. The feed separation unit 302 may be used to separate the feed into a vapor product and a solid/liquid product. Examples of equipment suitable for separating the vapor product from the liquid product include a knockout drum (e.g., substantially any vapor-liquid separator), a flash drum, distillation column/unit, flash drum having a heating means within the drum, a knockout drum having a heating means within the knock-out drum, and combinations thereof. During separation, the temperature of the feed separation unit 302 is maintained between 50° C. to 750° C. or preferably 100° C. to 515° C., which may be adjusted to control the separation level within the feed separation unit 302. Depending on the hydrocarbon feed, the vapor product may be readily separated from the remaining non-volatiles. Without separation, the solid/liquid product of the hydrocarbon feed may foul downstream lines or units. The solid/liquid product, which may include non-volatiles, may be withdrawn or removed from the feed separation unit 302 as a bottoms product or stream via line 323, which may be further processed or utilized for fuel for the thermal pyrolysis reactor 304 or other units. The vapor product, which is the pyrolysis feed, may be withdrawn from the feed separation unit 302 as an overhead stream via line 325 and passed to the thermal pyrolysis reactor 304.

The thermal pyrolysis reactor 304, as noted above, may include a regenerative reverse flow reactor or other suitable reactor. Accordingly, the thermal pyrolysis reactor 304 may have different piping configurations to provide combustion feed (e.g., fuel) and the pyrolysis feed separately, depending on the specific configuration.

The reactor effluent or reactor product from the thermal pyrolysis reactor 304 is conducted away via line 327 to the solid removal unit 306 and other recovery stage units. The solid removal unit 306 may include water scrubbing, oil scrubbing, cyclone separation, electrostatic separation, filtration, and/or moving bed adsorption. As may be appreciated, each of these systems may be combined together in one or more units to overcome certain limitations within the system. For instance, water scrubbing is effective to remove solid carbon black and other solids, but it limits the recovery of heat in the effluent. Oil scrubbing may be utilized for heat recovery, but it may present problems with fouling and emulsion formation. Cyclone separation may be limited to remove solid carbon, but not other smaller or fine solids. Electrostatic separation may have problems with clogging and short-circuiting due to carbon deposit buildup. Adsorption and filtration are limited to handling small amounts of solids and may be problematic for larger amounts of solids. As a result, one or more of these techniques may be coupled together in series to provide the appropriate separation. The solid-liquid phase of the reactor product from the reactor may be conducted away from solid removal unit 306 as a bottoms product, which may be a bottoms stream, via line 329. The bottoms product may include carbon black, soots, and/or heavy aromatic oils and/or tars. If the bottoms product is "dry", it may be handled via filtration or electrostatic separation. If sticky or wet, it may be handled via washing (oil or water) or absorption. The bottoms product may be recycled to the thermal pyrolysis reactor or may be used as a fuel in the thermal pyrolysis reactor or for other units. The remaining reactor product may be withdrawn from solid removal unit 306 as an overhead stream via line 331 and passed to the compressor 308.

The compressor 308 may receive the remaining reactor product from the solid removal unit 306 and compress the product to provide a compressed product via 333 to the product separation unit 310. The compressor 308 may compress to the vapor product to a pressure from 50 psig (345 kPag) to 400 psig (2758 kPag), or more preferably from 150 psig (1034 kPag) to 300 psig (2068 kPag). For other embodiments, the pressure may be adjusted for hydrogen ($H_2$) removal (e.g., pressure swing adsorption, hydrogen membrane and/or cryogenic distillation, electrochemical separation) and acetylene hydrogenation.

Once compressed, different products, such as different light gases or heavy products may be separated from the compressed reactor product in the product separation unit 310. The product separation unit 310 may include the different units discussed above along with caustic wash, amine scrubber and/or other treatments, which may also include steps to remove different products (e.g., $CO_2$, $H_2S$ and/or $H_2O$) from the process. For instance, carbon dioxide can be removed by washing the reactor product. This step may also include drying to remove entrained water. The remaining reactor product may be recovered from the product separation unit 310 as via line 335 and passed to the acetylene converter 312, while the impurities may be withdrawn as products or bottom streams via line 337, which may be further processed for the different impurities.

Optionally, the acetylene converter 312 may receive the remaining reactor product (e.g., acetylene-rich product or $C_2U$ products comprising acetylene and ethylene) from the product separation unit 310. The acetylene converter (A/C) selectively hydrogenates the acetylene to ethylene without significantly hydrogenating the ethylene to ethane. The acetylene converter may operate at feed levels ranging from 0.5 to 15 mol % acetylene. The acetylene converter may operate at pressures from 32 psig (221 kPag) to 400 psig (2758 kPag), at inlet temperatures of 50° C. to 300° C. and may utilize catalyst comprising group VI or VIII catalysts. Conversion levels for the hydrotreater may range from 70 wt % to 100 wt % acetylene conversion and may have selectivity to ethylene from 70 wt % to as high as 98 wt % to ethylene. The acetylene converter 312 may include an optional finishing acetylene converter to convert remaining levels of acetylene at 100 wt % conversion of the acetylene. This finishing acetylene converter may be in fluid communication with the one or more units, such as the acetylene converter 312 or other units downstream of the acetylene converter 312. The acetylene converter 312 may include a hydrogenation unit, and optionally may further include a compressor, stream recycle components, desorption unit and/or separation unit.

In one embodiment, a conversion product of ≥50 wt % of ethylene may be conducted away from the acetylene converter 312 to storage or for further processing. As an example, the conversion product may be passed to the purification unit 314 via line 339. The purification unit 314 may include a demethanator tower (to remove $H_2$, $CH_4$, $N_2$ and CO) and a $C_2$ splitter to remove ethane and upgrade ethylene to polymer grade ethylene. The purification unit 314 may also include $C_2$ or $C_3$ refrigeration train, compression and additional distillation towers. This purification unit 314 may separate the conversion product from the acetylene converter 312 into one or more products and an upgraded product, such as an ethylene stream. The one or more products, which are provided to line 341, may include different light gas products (e.g., hydrogen, carbon monoxide, nitrogen, methane, and the like) or heavier products (e.g., ethane and $C_{3+}$ streams). A portion of the recovered products may be recycled for processing again in the thermal pyrolysis reactor, such as methane and/or hydrogen. Further, if the conversion product is an ethylene stream, it may be provided to the ethylene polymerization unit 316 via line 343.

The ethylene polymerization unit 316 may be a catalytic reactor, which may include a gas catalyst and/or a liquid catalyst. The process may involve a catalyst, solvent and the feed stream, as discussed above.

In some embodiments, a portion of the acetylene in the reactor product may optionally be combined with other process steps to form other products. In particular, the portion of the acetylene may be an intermediate product or precursor in a process within a chemical plant, in route to other preferred products, such as vinyl esters, ethylene, acetaldehyde, propanal, propanol, acrylic acid, and/or the like.

In one or more embodiments, the hydrocarbon feed may be separated into a pyrolysis feed and a bottom stream prior to being provided to the thermal pyrolysis reactor. That is, the noncombustible nonvolatiles, such as metals and/or ash, may be managed by conducting away these products from the hydrocarbon feed prior to the thermal pyrolysis. As such, this configuration is able to receive advantaged feeds and process them in an efficient manner to produce olefins.

Figure 4:
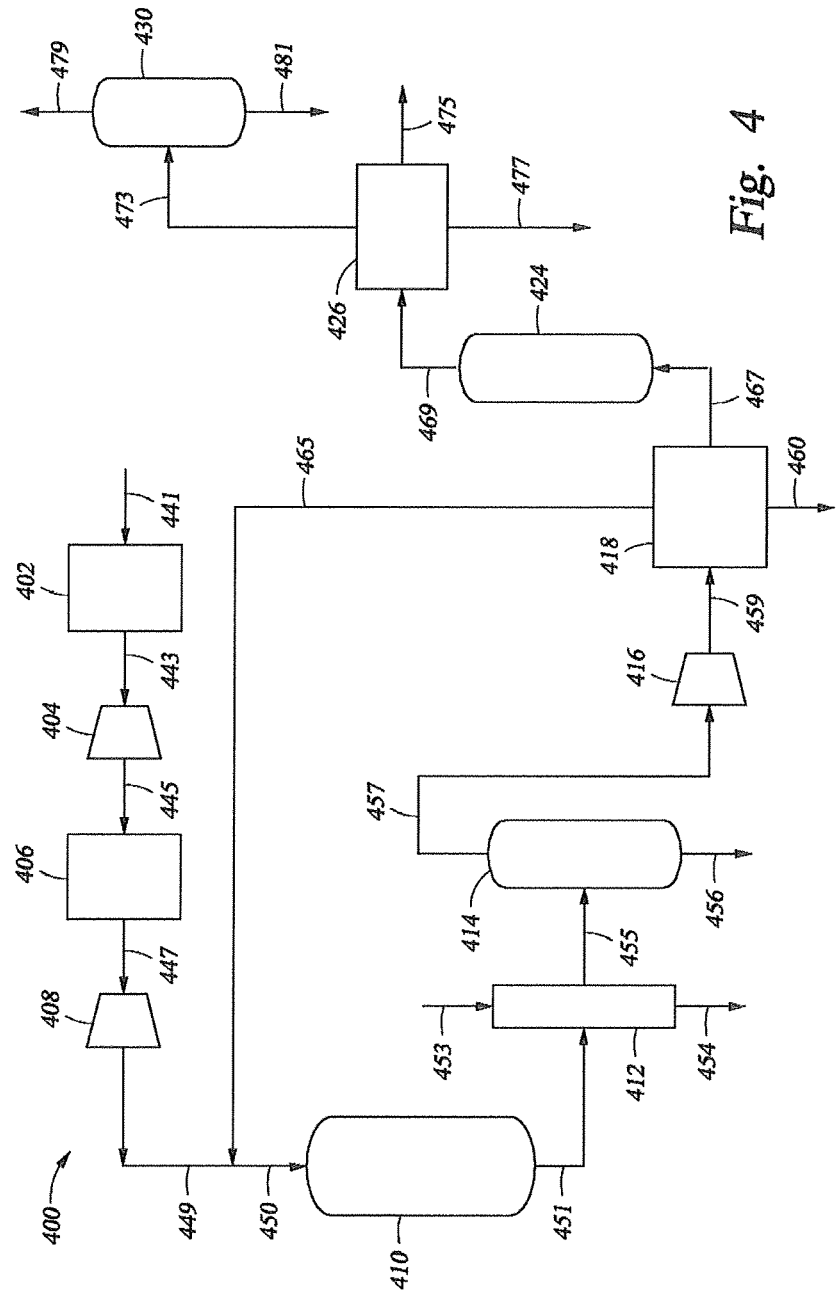
FIG. 4 is a simplified diagrammatic illustration of another exemplary process for converting the hydrocarbon feed to polyethylene in accordance with an embodiment of the present techniques.

FIG. 4 is a simplified diagrammatic illustration of another exemplary process to convert a hydrocarbon feed, such as natural gas, to a product, such as polyethylene, in accordance with an embodiment of the present techniques. In this illustration 400, a particular configuration of units are coupled together to convert hydrocarbon feed to a product, such as polyethylene. In this configuration, the feed preparation stage may include an acid gas removal unit 402, a first expander 404, a recovery unit 406, a second expander 408, while the cracking stage may include the thermal pyrolysis reactor 410. The recovery stage may include a heat exchanger 412, a solid removal unit 414, a compressor 416, a product separation unit 418, an acetylene converter 424 and a purification unit 426. The polyethylene polymerization stage may include the ethylene polymerization unit (not shown). In addition, in this configuration, a power conversion stage is also provided, which may include a nitrogen splitter unit 430. Various piping may be utilized to couple these units together, as discussed below. Further, similar to the discussion related to FIGS. 2 and 3, various units in this configuration may operate and function in a substantially similar manner to the units noted above in FIGS. 2 and 3.

To begin, a hydrocarbon feed may be provided via line 441 to an acid gas removal unit 402. The hydrocarbon feed may be raw natural gas, for example. The acid gas removal unit 402 may be configured to separate $H_2S$ and/or $CO_2$ products along with other sulfur species products from the hydrocarbon feed. The products may be provided to storage or conducted away from the process for further processing (not shown).

Then, the feed or stream is provided from the acid gas removal unit 402 via line 443 to the first expander 404. The first expander 404 may be used to depressurize the stream. For example, the stream may be expanded from a first or initial pressure of the hydrocarbon feed from the well to the gas plant pressure (e.g., nominally ≥1000 psig (6895 kPag) to the pressure utilized for natural gas liquid (NGL) separation (e.g., 200 psig (1379 kPag)). The expanded stream may be provided via line 445 to the recovery unit 406. The recovery unit 406 may be used to separate natural gas condensates or NGLs (e.g., $C_{3+}$) products from the stream. The products may be provided to storage or conducted away from the process for further processing (not shown). Again, the stream may be provided to an optional second expander 408 via line 447. The second expander 408 may further depressurize the stream from 200 psig (1379 kPag) to the thermal pyrolysis reactor pressure, which may include pressures in a range from 3 psig (21 kPag) to 200 psig (1379 kPag).

The expanded stream may then be provided to the thermal pyrolysis reactor 410 via lines 449 and 450. The expanded stream may be the pyrolysis feed or may be combined with a recycle stream 465 that include methane, hydrogen or a combination thereof to form the pyrolysis feed. Similar to the discussion above, the thermal pyrolysis reactor 410 may include any of a variety of reactors, such as a regenerative reverse flow reactor. Once cracked, the reactor product or reactor effluent from the thermal pyrolysis reactor 410 may be further processed in the recovery stage.

In the recovery stage, at least a portion of the reactor product may be passed to the heat exchanger 412 via line 451. The heat exchanger 412 may cool the reactor product from the reactor sufficiently for compression. That is, the heat exchanger 412 may cool the reactor product from the reactor to a temperature in the range of 50° C. to 400° C. or more preferably from 100° C. to 250° C., and utilize the reactor product along with a utility fluid to recover heat from the process for use in this or other processes. In certain embodiments, the heat exchanger 412 may use indirect heat transfer to cool the reactor product from the reactor and minimize the addition of contaminates. In this embodiment, the reactor product from the reactor may pass through the process side of a transfer line heat exchanger (TLE), while a utility fluid may be provided to the TLE via line 453 and exit the TLE via line 454. In this manner, the reactor product from the reactor is maintained separate from the utility fluid, which may include boiler feed water, the hydrocarbon feed, the pyrolysis feed or other suitable fluid. By utilizing this TLE, the process may enhance the energy efficiency of the process or facility.

The cooled reactor product may then be provided to solid removal unit 414, which may be similar to the solid removal unit 306 of FIG. 3, via line 455. In the solid removal unit 414, a bottom product comprising solids and/or tars may be separated from the cooled reactor product via one or more different mechanisms. For instance, in an oil wash unit, quench oil is mixed with the cooled reactor product to remove solids and/or tars from the cooled reactor product. For a cyclone unit, the remaining reactor product is introduced into the vessel and the bottoms product having solids flow to the bottom, while the remaining reactor product flows out another outlet. As may be appreciated, different combinations of these units may be coupled together in series to form the solid removal unit 414. From the solid removal unit 414, a bottoms product (e.g., bottoms stream) may be provided for further processing via line 456.

Then, the remaining reactor product may be further cooled, dried and provided to the compressor 416 via line 457. That is, a second heat exchanger or cooler may cool the remaining reactor product from the solid removal unit 414 to a temperature in the range of −50° C. to 100° C. The compressor 416, which may operate similar to the compressor 308 of FIG. 3, may be used to pressurize the stream to 50 psig (345 kPag) to 400 psig (2758 kPag), depending on the subsequent processing step. In certain embodiments, the compressor may not be utilized if the pressurized reactor product is maintained through the process at the appropriate pressure.

The pressurized reactor product may then be provided via line 459 to the product separation unit 418. The product separation unit 418 may separate different products from the remaining reactor product, such as light gas products or heavy products, for example. These products may be conducted away as one or more light gas products that include components that are lighter than $C_2$ hydrocarbons, or one or more heavy products that include components that are heavier than $C_2$ hydrocarbons. Lighter than $C_2$ components may include hydrogen, methane and any combination thereof, while heavier than $C_2$ components may include $C_{3+}$ products, such as methyl acetylene or benzene. These light gas products may be completely or only partially removed from the remaining reactor product in the product separation unit 418. The one or more of the different light gas products, such as hydrogen or other gases, may be recycled via line 465 or may be utilized in other units (not shown). The recycle product provided via line 465 may contain small amounts of acetylene and/or ethylene due to inefficiency of the separations. The acetylene-rich product (e.g., remaining portion of the reactor product after the one or more separations) may be passed via line 467 to the acetylene converter 424, which may operate similar to the acetylene converter 312 of FIG. 3. Separated heavy products (e.g., benzene) may be passed via line 460 for storage, for further processing in other units (not shown), or may be recycled to the thermal pyrolysis reactor 410 as pyrolysis feed or as combustion fuel.

The acetylene-rich product may be processed in the acetylene converter 424 to form a conversion product that is provided via line 469 to purification unit 426, which may operate similar to the purification unit 314 of FIG. 3. The purification unit 426 may include a demethanator tower (to remove hydrogen ($H_2$), methane ($CH_4$), nitrogen ($N_2$) and carbon monoxide (CO)), a $C_2$ splitter to remove ethane and purify ethylene to polymer grade ethylene, or a $C_2$ or $C_3$ refrigeration train, compression and additional distillation tower. The ethylene product, which may be provided from line 475, may be provided to the ethylene polymerization unit (not shown). However, in this configuration, the purification unit 426 may separate the conversion product into a fuel product, such as methane and lighter gases, provided via line 473 to nitrogen splitter unit 430 for power generation stage. As part of the power conversion stage, the optional nitrogen splitter unit 430 may separate a nitrogen product from the fuel product. From the optional nitrogen splitter unit 430, a nitrogen product may be provided via line 479 for storage or further processing, while the fuel product may be provided via line 481 to storage or for further use as fuel. Similarly, a heavier conversion product (e.g., saturated $C_2^+$ components, such as ethane and/or propane) may be separated in the purification unit 426, which may be provided via line 477 for storage or further processing. Optionally, the heavier conversion product may be utilized as a recycle product, or to be mixed with the output line 481 of the nitrogen splitter unit 430 for storage or further processing.

As a specific example, the configuration may be utilized to convert raw natural gas into polyethylene. In this example, the feed preparation stage may include an acid gas removal unit 402, a first expander 404, a recovery unit 406, a second expander 408, while the cracking stage may include the thermal pyrolysis reactor 410, which may be a regenerative reverse flow reactor. The recovery stage may include a heat exchanger 412, a solid separation unit 414, a compressor 416, a product separation unit 418, an acetylene converter 424, and a purification unit 426 (which may include a de-methanizer unit and an ethylene splitter unit). The polyethylene polymerization stage may include the ethylene polymerization unit (not shown). In addition, in this configuration, a power conversion stage may also be provided, which includes a nitrogen splitter unit 430. Various piping may be utilized to couple these units together.

In this embodiment, a hydrocarbon feed, such as raw natural gas, may be processed with the flexibility to manage or remove various components at different stages in the process. That is, non-methane components of the natural gas (e.g., impurities, such as natural gas liquid (NGL), ethane, LPG, $H_2S$, $CO_2$, $N_2$, and mercaptans) may be removed or managed in the process. For example, the NGL, ethane or liquefied petroleum gas (LPG) may be removed from the process to be sold as separate products. Alternatively, the NGL or mercaptans may be provided to the reactor and converted into acetylene or ethylene. Similarly, the other impurities, such as $H_2S$, $CO_2$, and $N_2$, may be separated as products prior to or after the thermal pyrolysis reactor. That is, unlike other processes, the present techniques utilize operating conditions and the thermal pyrolysis reactor to manage the impurities.

By providing this flexibility, the process may be integrated with a gas production facility at various locations because the thermal pyrolysis reactor and operating conditions provide enhancements for managing impurities. For instance, the acid gas removal unit 402, first expander 404, recovery unit 406, and second expander 408 may be units within a liquefied natural gas (LNG) facility or gas production facility. In this type of configuration, other products may be separated from the natural gas stream, while certain impurities may remain within the pyrolysis feed provided to the reactor because certain impurities are expensive to separate, such as nitrogen. Further still, in certain embodiments, the feed may be processed to remove certain products or streams, which may be used for fuel. The fuel product may be provided to storage or may be provided via recycle products to the thermal pyrolysis reactor, to power generation units, or to other equipment within the gas production facility. As a specific example, the products from lines 456, 460 and 477 may be recycled to the thermal pyrolysis reactor 410 or a gas production facility as feed and/or fuel. As such, the present techniques provide flexibility in coupling with other processes, such as a gas production facility (e.g., an LNG facility, gas plant or similar facility), which provide capital savings by reducing the units utilized to process raw gas feeds.

Although the units of FIGS. 3 and 4 are shown as respective single and separate units, each of these units can alternatively comprise a plurality of units. For example, a separation unit may include more than one knockout drums, separators, and/or flash drums. Accordingly, different embodiments may utilize different units in this manner. Further, some additional embodiments, which are discussed further below, may be utilized in these embodiments of FIGS. 2 to 4.

In certain embodiments, the thermal pyrolysis reactor may be operated at different pressures to further enhance the operation of the system. For example, in some embodiments, the pyrolysis of volatized hydrocarbons may occur at different pressures, such pressures ≥36 psig (248 kPag), ≥44 psig (303 kPag) or ≥103 psig (710 kPag), but the pressures may be ≤300 psig (2068 kPag), ≤163 psig (1124 kPag), or ≤150 psig (1034 kPag), or different combinations thereof. Pressures higher or lower than that disclosed above may be used, although they may be less efficient.

Each of the thermal pyrolysis reactors may be operated at different temperatures based on the specific operation and process variations. The different thermal pyrolysis reactors may include specific mechanisms and processes to heat the pyrolysis feed. Accordingly, each reactor may include different means for measuring the temperature of that specific process.

As a specific example for a thermal pyrolysis reactor, the pyrolysis stream is heated by a solid material, which is heated by a combustion reaction. Usually, the solid material forms the channels that the pyrolysis stream travels through. The combustion reaction of combustion feed that heats the solid material may heat via convective and/or radiative mechanisms. In these reactors, the highest temperatures are observed in the stream that is heating the solids (e.g., combustion stream). At any location, the solid material has a temperature that is lower than that of the combustion stream from which it receives heat, while the pyrolysis stream being heated by the solid material has a temperature that is lower than the solid material. The specific temperature of the combustion stream, pyrolysis stream or solid material depends on its location within the reactor and on the configuration and/or operation of the pyrolysis reactor.

In certain thermal pyrolysis reactors (e.g., steam cracking furnace configuration), the heating and the pyrolysis process occur simultaneously, for example with a combusting stream on one side of the partition (typically a wall or tubular) and the pyrolysis stream on the other side. Such reactors operate at or near steady state. The partition between the combustion feed and the pyrolysis feed has physical dimensions and the temperature is not equal at every location. For example, on the combustion side, temperatures may be hottest near a flame region, and on the pyrolysis side temperatures increase with heat addition until some maximum temperature is reached. Steady state in these systems means that, at any given location relative to the fixed partition, temperatures remain relatively steady. However, the gases that travel through the reactor are heated and cooled by the chemistry and heat transfer that takes place in the reactor. The term "peak pyrolysis gas temperature" means the maximum temperature achieved by the bulk pyrolysis stream gases as they travel through the pyrolysis reactor (e.g., cracking region or radiant region). One skilled in the art will appreciate that temperatures immediately proximate to the partition may be higher, and may, in some infinitesimal layer, actually approach the solid temperature. However, the pyrolysis temperature referred to herein should be considered a bulk gas temperature, which is a temperature that could be measured by a device (such as a thermocouple) that is not in contact with the solid material. For example, if the gas is traveling through tubulars in a thermal pyrolysis reactor, the bulk gas temperature may be taken as the average temperature over any tubular cross-section, and the peak pyrolysis gas temperature as the highest cross-sectional-average temperature of the pyrolysis stream.

In a thermal pyrolysis regenerative reactor system, the heating and pyrolysis occur in sequential steps. First, a heating step, usually a combustion reaction or combustion step, is used to heat the solid material. Second, a pyrolysis step is carried out that absorbs heat from the solid material to effect a chemical reaction. The solid material may be in fixed orientation or in moving orientation. If moving, the solid is typically moved from a heating region to a pyrolysis region. Moving-solid systems appear to be step-wise from the perspective of the moving solid, however the gas streams may be at steady state in any absolute location, and temperatures are defined very much as discussed for thermal pyrolysis furnace-type reactors. When the solid material is in fixed orientation, a regenerative system may use valves to alternate introduction of a pyrolysis and heating streams into the solid-containing region. The solid material may be designed to facilitate the process of heat addition and removal. Checker bricks, tiles and monoliths may be used as the solid materials within the reactor. Such materials form a network of passages that are used by the gases in each step to transit the region containing solid material. The heat addition step leaves a profile of temperatures in the solid material, that is, a temperature that varies along the path by which the gases transit the solid material. The shape of that profile depends on many factors, including if and where a heat release (combustion) reaction occurs, the initial temperature distribution, the duration of the heating step, the flow rate and inlet temperature of the gas stream, and the heat capacity and transfer properties of the gas and solid material. On average, the solid material is hottest at the end of the heating step. The pyrolysis step consumes heat and reduces average solid material temperature. The pyrolysis step changes the profile of temperatures in the solid material, in a way that depends on many factors, including where the heat consumption (pyrolysis) reaction occurs, the initial temperature distribution, the duration of the pyrolysis step, the flow rate and inlet temperature of the gas stream, and the heat capacity and transfer properties of the gas and solid. Fixed-solid regenerative pyrolysis reactors are not at steady state. That is, at any given location, the temperature changes. However, these reactors may be in a periodic steady state, meaning that the same cycling of temperatures occurs over and over as the reactor oscillates between heating and pyrolysis.

In a reverse-flow regenerative system, a reversal occurs in the direction of transit of the gases through the region that contains the solid material, and this reversal occurs in between the heating and pyrolysis steps. In some embodiments, reversal occurs between every step, and in other embodiments reversal occurs in alternating step changes. Regardless, the flow reversal enables substantial heat exchange between the incoming gas of one step and the outgoing gas of the alternate step. This results in a reactor that has highest temperatures near the middle of the flow path, and relatively cool temperatures at both ends of the reactor.

In a regenerative pyrolysis system, peak pyrolysis gas temperature is determined as follows. The peak pyrolysis gas temperature typically is experienced by the gases at the beginning of the pyrolysis step, because the solid material is typically at its highest temperature at the beginning of the pyrolysis step. One skilled in the art will appreciate that temperatures immediately proximate to the solid material may be higher, and may, in some infinitesimal layer, actually approach the solid temperature. However, the pyrolysis temperature referred to herein should be considered a bulk gas temperature, which is a temperature that may be measured by a device (such as a thermocouple) that is not in contact with the solid material. For example, if the gas is traveling through channels in a checkerbrick, tile or honeycomb solid material, the bulk gas temperature could be taken as the average temperature over any channel cross-section, and the peak pyrolysis gas temperature as the highest cross-sectional-average temperature of the pyrolysis stream.

Thermal pyrolysis reactors may also be characterized in terms of the residence time of pyrolysis gases in the reactor. Residence time is most generally defined as the time required for some average non-reacting molecule to pass through the pyrolysis reactor or furnace. Residence time may be further defined to be the time spent within the actively heated or cooled portions of the reactor or furnace. This includes time spent within tubulars or heat transfer solids of a furnace or regenerative reactor, respectively, but excludes residence time spent in headers or other means of conveyance to or from the actively heated or cooled regions of the furnace or reactor. Additionally, the high-severity residence time is defined as the time that pyrolysis stream components are exposed to temperatures above the severity threshold. An exact calculation of residence time requires measurements with tracer compounds (such as radioactive additives to the feed) or requires a specific knowledge of the temperature and composition of the pyrolysis stream at all times as it passes through the pyrolysis reactor. For the purposes of the present application, residence time (in either form) may be approximated using interpolation and extrapolation of discreet composition and temperature measurements, and/or using model-based estimations of temperature and composition, as is known in the art.

In addition to the operating pressure, the one or more embodiments may include the conversion of feedstocks into higher value hydrocarbons, such as acetylene, at different temperatures. These temperatures may include high reformation temperature, which in the past has been a significant barrier to commercialization and efficiency. The pyrolysis reactor according to the present techniques is a higher temperature hydrocarbon pyrolysis reactor that operates at higher temperatures than steam cracking reactors used in commercial steam cracking operations. For example, naphtha steam cracking operations typically operate at furnace radiant coil outlet temperatures of ≤about 815° C., which corresponds to the peak pyrolysis gas temperature. However, in the present techniques, the thermal pyrolysis reactor may operate at peak pyrolysis gas temperatures between 1200.0° C. and 2200.0° C., preferably between 1400.0° C. and 1900.0° C. In particular, for reactors with an isothermal heat profile, the temperatures may be between 1450.0° C. and 1700.0° C., or between 1540.0° C. and 1650.0° C. For reactors with a Gaussian like heat profile, the peak pyrolysis gas temperatures may be between 1450.0° C. to 1900.0° C. or 1540.0° C. to 1800.0° C. In some reactions, it may even be still more preferable to expose the pyrolysis feed to heat using very short residence times, such as ≤0.1 second, to a temperature in excess of 1600.0° C. Pyrolysis reactions that benefit from reaction or conversion of methane that may be a part of the pyrolysis feed, typically involve peak pyrolysis gas temperatures in excess of 1400.0° C. for the methane to react or convert. An exemplary preferred process may pyrolyze the feed stream within the reactor, such as at peak pyrolysis gas temperatures of from 1540.0° C. to 2200.0° C., and more preferably from 1600.0° C. to 1800.0° C. Exemplary residence times preferably may be short, such as ≤0.5 second, ≤0.3 second and preferably ≤about 50 milliseconds or in the range of 0.5 seconds to 0.001 seconds. High severity residence times are preferably ≤0.05 seconds, and more preferably ≤0.02 seconds.

As described earlier, achieving any peak pyrolysis gas temperature involves the existence of a solid temperature that is heated to a higher temperature, and a combustion gas temperature that is a higher temperature than the solid temperature. In one or more embodiments of the present techniques, the maximum temperature of the solid elements in the thermal pyrolysis system (e.g., tubulars for furnaces or heat transfer solids for regenerative systems) is between about 5° C. and about 500° C. higher than the peak pyrolysis gas temperature. In a preferred embodiment, the maximum temperature of the solid elements in the thermal pyrolysis system is between 10° C. and 100° C. higher than the peak pyrolysis gas temperature. Reverse flow regenerative reactors may also include some amount of quenching by means of heat removal to the heat transfer solids. In reverse flow regenerative reactor embodiments of the present techniques, the pyrolysis gas may be cooled to a temperature between 100° C. and 1000° C. by means of heat removal to the heat transfer solids in the reactor, and more preferably cooled to a temperature between 300° C. and 550° C.

In one or more embodiments, the pyrolysis feed may be derived from different hydrocarbon feeds or mixtures thereof. For instance, the pyrolysis feed may include methane, which may be part of a natural gas stream. This feed, including associated hydrocarbon and impurity gases, may be supplied into the reactor system. The supplied feed may be sweetened and/or dehydrated natural gas. Natural gas commonly includes various concentrations of associated gases, such as ethane and other alkanes, preferably in lesser concentrations than methane. The supplied natural gas may include impurities, such as hydrogen sulfide $H_2S$ and nitrogen. Certain embodiments may also serve to simultaneously convert some fraction of the associated higher hydrocarbons to acetylene. In other embodiments, the present techniques and compositions may be utilized with liquid feeds, such as vacuum gas oil (VGO) or naphthas. In one or more embodiments, the pyrolysis feed is advantageously pyrolyzed with an overall hydrogen content of the hydrocarbons in the pyrolysis feed in the reactor pyrolysis-stage that is ≥10 wt %, preferably ≥12 wt %, and more preferably ≥15 wt %. Further, in other embodiments, the hydrocarbon feed may be a mixture of heavy hydrocarbon feed and methane, having aggregate hydrogen content≥15 wt %. This adds the flexibility of controlling the $H_2$ byproduct. If $H_2$ is valued at a fuel or feed value, a lower hydrogen content feed may be used to maximize the chemical product value; or if hydrogen ($H_2$) is valued at chemical value (methane steam reforming value), higher hydrogen content feeds may be preferred (to meet chemical value $H_2$ demand). This also adds feed flexibility to crack liquids when gas prices are high (relative to crude) and gas when liquid prices are high relative to gas.

In other embodiments, the thermal pyrolysis reactor may be a regenerative reverse flow reactor or regenerative pyrolysis reactor. Regenerative pyrolysis reactors are well suited for processing volatized or volatizable feedstocks that are substantially free of non-volatile components, such as metals, and other residual or nonvolatizable components, which would otherwise lay down, ash, and/or build up in the reactor. Examples of such reactors may be found in U.S. Patent Application Publication Nos. 2007/0144940 and 2008/0142409. These references, which are incorporated by reference, teach a regenerative bed reverse flow reactor wherein the location of the exothermic reaction is controlled. The regenerative reactor bed is regenerated by supplying a first reactant through a first channel to a first regenerative bed and a second reactant through a second channel in the first regenerative bed, combining first and second reactants in a gas mixer, and reacting to produce a heated reaction product which is passed through a second regenerative bed to transfer heat thereto. Other examples may be found in U.S. Patent Application Publication Nos. 2009/0008292 and 2009/008292; U.S. Pat. No. 7,491,250 U.S. Patent Application Publication No. 2009/008292; and U.S. Patent Application Ser. No. 61/349,464, which are each incorporated by reference.

As an example, U.S. patent application Ser. No. 11/643, 541 (U.S. Patent Application Publication No. 2007/0191664), which is incorporated by reference, describes a process and high severity regenerative thermal pyrolysis reactor utilized to manufacture acetylene from a methane or hydrocarbon-containing feed. These process steps and/or pyrolysis reactor may be utilized in one or more of the embodiments described above. For instance, the process may include a reactor system that includes (i) a first (quenching) reactor comprising a first end and a second end, and (ii) a second reactor comprising a primary end and a secondary end, the first and second reactors oriented in a series relationship with respect to each other such that the secondary end of the second reactor is proximate to the second end of the first reactor. The process may include a two-step process wherein heat is: (1) added to the reactor media via in-situ combustion step and (2) removed from the reactor media via in-situ endothermic pyrolysis step. The combustion step may involve passing a first and second combustion reactant (combustion feeds) separately but simultaneously through the first (quenching) reactor, by supplying a first reactant through a first channel in the first reactor and supplying at least a second reactant through a second channel in the first reactor, such that the first and second reactants are supplied to the first reactor from the first end of the first reactor. The combustion step may further involve combining the first and second reactants at the second end of the first reactor and reacting the combined reactants to produce a heated reaction product; passing the heated reaction product through the second reactor to transfer at least a portion of the heat from the reaction product to the second reactor, and recovering an exhaust gas from the second reactor. Preferably, the combining is enhanced by a reactant (combustion feed) mixer that mixes the reactants to facilitate substantially complete combustion/reaction at the desired location, with the mixer preferably located between the first and second reactors. Thereafter, the endothermic pyrolysis step supplies methane or other hydrocarbon through the heated second reactor to the first reactor, in flow direction the opposite to that of the heating (combustion) step, to convert at least a portion of the methane into acetylene; passing the supplied methane and the produced acetylene through the first reactor to quench the methane and the produced acetylene; and recovering the produced acetylene. The process may further include supplying hydrogen in the second reactor during the pyrolysis step to moderate the reaction of the methane or other hydrocarbons in the feed. Hydrogen may be used in molar ratio to methane of 0 to 5, preferably of 1 to 3 during the pyrolysis step. In a preferred embodiment, the media in the first reactor includes one or more honeycomb monolith structures that provide flow channels for the first and second reactant. The process may further include media of the first or second reactor that has wetted surface area between 50 and 3000 ft$^{-1}$, heat transfer coefficient≥0.02 cal/cm$^3$s° C., and bulk heat capacity ≥about 0.10 cal/cm$^3$° C., and may be comprised of honeycomb monoliths having 40 to 80% open frontal area and between about 50 and 2000 channels per square inch. The process may further include compressors, blowers, or fans to supply air as one combustion feed during the combustion step, which may be carried out at different pressures, which may be substantially similar in the pyrolysis step or at a different pressure; may include expansion turbines to recover mechanical energy from higher pressure exhaust gases; and may include recycle of exhaust gases (EGR) to the combustion feed for combination with the air, for example to reduce the oxygen content and the adiabatic flame temperature of the combustion feed. Noncombustible gases, for example $H_2O$, $CO_2$, and $N_2$, may be added to the combustion feed to reduce combustion temperature. The combustion step may comprise a first and second reactant that are a fuel gas and an oxidant that are maintained substantially separated as they pass through the first reactor and which combust or burn when combined. Substantially separated is meant that at least 50%, and more preferably 75% or 90% of the potential combustion that may occur will occur after the axial transit of the first reactor. The process may further include a mixer that is comprised of multiple mixer segments, each preferably having similar cross-sectional area and length and each preferably accepting flow during the combustion step from roughly equal numbers of first and second channels, representing roughly equal proportions of first and second reactant, and having a characteristic L/D between 0.1 and 5.0. Preferably, the mixer has a total volume≤20% of the total volume of mixer plus flow regions in the first and second reactor, and preferably has a geometric void volume≤20% of the void volume in mixer plus first and second reactor. The process may further include a cycle time that includes the time spent in combustion step plus time spent in pyrolysis step plus any time needed to switch between steps. Typical cycle times may be between 1 and 240 seconds, or between 2 and 60 seconds, and without expectation that combustion and pyrolysis steps will have equal durations.

As an example, U.S. Ser. No. 12/119,762, which is incorporated by reference, describes a process and regenerative pyrolysis reactor utilized for pyrolyzing a hydrocarbon feedstock containing nonvolatiles. These process steps and/or pyrolysis reactor may be utilized in one or more of the embodiments described above. For instance, the process may include heating the nonvolatile-containing hydrocarbon feedstock to a temperature sufficient to form a vapor phase that is essentially free of nonvolatiles and a liquid phase containing nonvolatiles; separating the vapor phase from the liquid phase; feeding the separated vapor phase to the regenerative pyrolysis reactor system; and converting the separated vapor phase in the regenerative pyrolysis reactor system to form a pyrolysis product. Further, the process may include quenching the converted separated vapor phase to form the pyrolysis product; may include heating the nonvolatile-containing hydrocarbon feedstock to a temperature in the range of from about 200° C. to about 650° C.; may include feeding at least one of a diluent and a stripping agent to the pyrolysis reactor system while transferring the at least a portion of the separated vapor phase to the pyrolysis reactor system for cracking the vapor phase in the presence of the at least one of the diluent and the stripping agent within the pyrolysis reactor system, wherein the at least one of the diluent and the stripping agent comprises at least one of hydrogen and steam; may include heating of the hydrocarbon feedstock via at least one of a heat exchanger, steam injection, and a fired heater.

As another example, U.S. patent application Ser. No. 12/121,353, which is incorporated by reference, describes a process and regenerative pyrolysis reactor utilized for pyrolyzing a hydrocarbon feedstock containing nonvolatiles. These process steps and/or pyrolysis reactor may be utilized in one or more of the embodiments described above. For instance, this process heating the nonvolatile-containing hydrocarbon feedstock upstream of a regenerative pyrolysis reactor system to a temperature sufficient to form a vapor phase and a nonvolatile-containing liquid phase; separating the vapor phase from the liquid phase; feeding the separated vapor phase and methane to the regenerative pyrolysis reactor system; and converting the separated vapor phase in the regenerative pyrolysis reactor system to form a pyrolysis product. The process may further include the separated vapor phase that is substantially free of nonvolatiles; may include quenching the converted separated vapor phase to form the pyrolysis product; or may heat nonvolatile-containing hydrocarbon feedstock to a temperature in the range of from about 200° C. to about 650° C. The heating of the hydrocarbon feedstock may be carried out by at least one of a heat exchanger, steam injection, the reactor system, a fired heater, and combinations thereof upstream of a regenerative pyrolysis reactor system.

As another example, U.S. Patent Application Ser. No. 61/349,464, which is incorporated by reference, describes a process and regenerative pyrolysis reactor utilized for pyrolyzing a hydrocarbon feedstock. These process steps and/or pyrolysis reactor may be utilized in one or more of the embodiments described above. For instance, a reactor may include a reactor body, wherein the reactor body forms a reaction region within the reactor body; a packing material disposed within the reaction region; and one or more poppet valve assemblies coupled to the reactor body and in flow communication with the reaction region and controlling fluid flow between a location external to the reactor body and within the reaction region. Further, a reactor may include a reactor body; a first head engaged with the reactor body; a first conduit extending from outside the head to at least partially through the head; and a first valve in flow communication with the first conduit controlling fluid flow along a flow path extending from the first valve and through the reactor body. The reactor may further include a second head engaged with the reactor body; a second conduit extending from outside the first head or the second head to at least partially through the respective head; and a second valve in flow communication with the second conduit controlling fluid flow along the flow path including a portion extended from the reactor body to the second valve; may be configured wherein the first valve has a substantially open position when fluid flow in the flow path is in a first flow direction and a substantially closed position when fluid flow in the flow path is in a second, opposite flow direction; may have a first valve pair on opposite sides of at least a portion of the flow path, wherein the first valve and second valve are each in a substantially open position when fluid flow in the flow path is in a first flow direction and a substantially closed position when fluid flow in the flow path is in a second, opposite flow direction; may include a third conduit extending from outside the first head or the second head to at least partially through the respective head; a third valve in flow communication with the third conduit controlling fluid flow along the flow path including a portion extended from the reactor body to the third valve; a fourth conduit extending from outside the first head or the second head to at least partially through the respective head; and a fourth valve in flow communication with the second conduit controlling fluid flow along the flow path including a portion extended from the reactor body to the fourth valve; and may have a second valve pair comprising the third valve and the fourth valve on opposite sides of at least a portion of the flow path, controlling flow in the second, opposite flow direction wherein the third valve and the fourth valve are each in a substantially closed position when the fluid flow in the flow path is in the first flow direction and in a substantially open position when fluid flow in the flow path is in the second, opposite flow direction; may include one or more additional valves, each in flow communication with one of the first, second, third, or fourth conduits via an additional conduit extending at least partially through the additional conduit's respective head. operating in phase with any other valves in fluid communication with the additional conduit and controlling fluid flow along the flow path including a portion extended from the reactor body to the respective valve; may include a reactor bed, and the volume of the flow path consists of (i) a packed flow path volume within a solids-fluids contact portion of the reactor bed, and (ii) an open flow path volume between the valve(s) and the reactor bed, as well as any open flow portion within the reactor bed; may have a packed flow volume comprises all volume in the reactor bed that is at a distance≤2 cm from a solids-fluids contact surface; may have a solids-fluids contact portion of the reactor bed having a wetted area≥0.5 $cm^2/cm^3$ in all regions of the portion of the reactor bed; may have a ratio of the open flow path volume to packed flow path volume is ≤1; may have a ratio of the open flow path volume to packed flow path volume is ≤0.5; may include a reactor bed that has a fixed bed core comprising solid material capable of heat exchange; may include at least one of the valves is a poppet valve comprising a disk element connected to a valve stem element; may have a distance during operation between the poppet valve disk element flat surface in the fully open position and the reactor bed surface is between 5% and 200% of the disk element diameter; may have a distance during operation between the poppet valve disk element flat surface in the fully open position and the reactor bed surface is between 20% and 80% of the disk element diameter, may extend the poppet valve stem element to a location outside the head; may have each valve associated with an externally accessible valve seat that fits within its respective inlet to the reactor body and/or outlet from the reactor body and is sealed to the head, wherein the valve seat is attached to the head via one of a rotatable locking mechanism, thread-in seats, and pressed-in seats; may include a valve stem seal associated with the valve stem; may include a valve stem seal that is a reciprocating compressor-type seal, may include an actuator is at least one of pneumatically actuated, hydraulically actuated, and electromagnetically actuated.

In other embodiments, the use of a reverse flow regenerative reactor in the process may be utilized to remove other inefficiencies. That is, while certain embodiments may include heat exchangers for heat recovery, the quenching step is performed within the reactor as part of the process, not as a separate step. For instance, certain embodiments may avoid an active quench stage, as the reactor product from the reverse flow regenerative reactor is cooled passively prior to exiting the reactor. That is, an expensive water or oil quench tower for rapid temperature reduction may not be utilized with the different configurations above. Active quench systems include a separate unit or step outside the reactor, such as mixing water or oil with the stream, or expanding in a kinetic energy quench, such as a Joule Thompson expander, choke nozzle, or turbo expander. Unlike the active quench stage, the present techniques utilize the flow through the reactor to cool the reactor product. In this manner, the inefficiencies of a quench step are removed from this process because the effluent is passively quenched by flow within the reactor.

In one or more embodiments, heat recovery may be utilized within the system to further enhance the operation. For example, the outlet temperatures may be below 600° C., below 500° C., or in a range from about 200° C. to about 600° C., or more preferably from about 300° C. to about 500° C. Accordingly, heat exchangers, such as transfer line exchangers (TLEs) or shell and tube heat exchanger units may be used to recover heat between units or process steps.

Further, other embodiment may include a dilute acetylene stream, which may be compressed with inter-stage cooling and drying as appropriate for a secondary conversion stage. The products are washed (caustic wash or amine scrubbing) to remove acidic species and impurities as necessary for the production of high purity polyolefin feed. The dilute acetylene is hydrogenated in an acetylene converter to yield dilute ethylene (advantageously, without the addition of a separate $H_2$ stream). The dilute ethylene is purified and traces of methane, ethane, residual acetylenes and CO are removed and the resulting high purity ethylene (polymer grade) is polymerized to polyethylene in a separate reactor.

In some other embodiments, the use of the materials may provide additional benefits in the selectivity of operations. For example, regenerative pyrolysis reactors generally have not been used commercially to temperatures above 1300° C. because of the alumina internals and the process, as noted in the references discussed above. In a regenerative reactor, which utilizes the materials noted herein, the operating temperatures within the reactor may reach temperatures up to 1500° C. to 2200° C. In this manner, the process may be operated at a higher conversion at high selectivity and reduce the overall capital cost of the process. That is, the process may produce fewer byproducts by operating at these higher temperatures.

Further, the temperature within the pyrolysis reactor may also involve large swings in temperatures. Accordingly, pyrolysis reactors materials have to be designed to withstand these temperature swings. That is, in the proposed configuration, pyrolysis reactors may have components or internals, such as valves, tubes, conductive monoliths, thin-walled honeycombs, bead-beds, mixers, quench media, and other reactor components, regardless of whether simple or complex shaped, that are directly associated with the pyrolysis reaction. These components are made of different materials able to withstand these larger temperature swings. As a specific example, a regenerative reverse flow reactor may include different materials for its internal components. That is, the components may be substantially formed from, predominately formed from or partially formed from certain materials, such as refractory materials (some of which are noted below). For instance, a regenerative reverse flow reactor may include a first reactor and a second reactor in flow communication with the first reactor, the first reactor comprising a first channel for conveying a first reactant through the first reactor to the second reactor and a second channel for conveying a second reactant through the first reactor to the second reactor, the first reactant exothermically reacting with the second reactant in the second reactor. Further, the reactor may include components, such as a honeycomb monolith, a reactor bed, a reactor conduit, and a reactant mixer, which is made completely from one of the materials, discussed or is made substantially from one or more of the materials. Certain of these components may have flow channels to provide passage for fluids through the components, such as a honeycomb monolith.

As an example, the reactor component, such as a monolith, may be made from (e.g., substantially, predominately or partially made from) a refractory material in oxide form, wherein the refractory material has a melting point of no less than 2060° C. and which remains in oxide form for at least one of: (i) when exposed to a gas having an oxygen partial pressure of $10^{-15}$ bar, a carbon partial pressure above the carbon partial pressure of the zirconium carbide and zirconium oxide phase transition at the same temperature, and at temperatures below the temperature of the zirconium triple point at the oxygen partial pressure of $10^{-15}$ bar; and (ii) when exposed to a gas having an oxygen partial pressure of $10^{-15}$ bar and at temperatures above the zirconium triple point at the oxygen partial pressure of $10^{-15}$ bar. An example of these materials may include U.S. Patent Application Publication Nos. 2009/0250377 and 2010/126907, for example.

As yet another example, U.S. patent application Ser. No. 12/467,832, which is incorporated by reference, describes a pyrolysis reactor having components or internals, which are exposed to heat within the reactor region, formed from refractory material that includes an yttria stabilized zirconia. These components or internals may be utilized in one or more of the embodiments described above. The refractory material comprising at least 21 wt % yttria based upon the total weight of the refractory material. In particular, the material may have a porosity at 20° C. in the range of from 5 to 28 vol. % based upon the volume of the refractory material; may include at least 25 wt % yttria based upon the total weight of the refractory material; may have a porosity at 20° C. in the range of from 5 to 25 vol. % based upon the volume of the refractory material; may include at least a first grain mode including yttria stabilized zirconia and a second grain mode comprising yttria; may include (i) at least 20 wt % of a first grain mode based upon the total weight of the refractory material, the first grain mode comprising yttria stabilized zirconia having a D50 grain size in the range of from 5 to 2000 μm, the first grain mode comprising at least 6 wt % yttria based upon the weight of the first grain mode, and (ii) at least 1 wt % of second grain mode based upon the total weight of the refractory material, the second grain mode having a D50 grain size in the range of from 0.01 μm up to not greater than one-fourth the D50 grain size of the first grain mode stabilized zirconia, the second grain mode comprising at least 14 wt % yttria based upon the weight of the second grain mode; may include at least one of yttria oxide, an yttrium containing compound, and combinations thereof; may include the refractory material comprises yttria and/or yttria stabilized zirconia, at least one of the yttria and/or the yttria stabilized zirconia having a D50 grain size in the range of from 0.01 to 2000 μm; may include at least 30 wt % yttria based upon the total weight of the refractory material; may have a porosity at 20° C. in the range of from 10 to 20 vol. % based upon the volume of the refractory material; may have from 0.001 wt % to 5 wt % based upon the weight of the refractory material, of compounds that comprise elements selected from the group consisting of Al, Si, Mg, Ca, Fe, Mn, Ni, Co, Cr, Ti, Hf, V, Nb, Ta, Mo, W, Sc, La, and Ce, and mixtures thereof. The first grain mode may include at least 14 wt % yttria based upon the weight of the first grain mode; or may include stabilized zirconia having a D50 grain size in the range of from 5 μm to 800 μm. The second grain mode comprises yttria fully stabilized zirconia; may consists essentially of yttria; may include at least 50 wt % of yttria fully stabilized zirconia comprising at least 14 wt % yttria, based upon the weight of the first grain mode; may include yttria fully stabilized zirconia, and excess the yttria is included within one or more of (a) the first grain mode, (b) the second grain mode, and (c) an optional another grain mode.

As still yet another example, U.S. patent application Ser. No. 12/772,757, which is incorporated by reference, describes a pyrolysis reactor having components or internals, which are exposed to heat within the reactor region, which formed from refractory material in oxide form. These components or internals may be utilized in one or more of the embodiments described above. The refractory material has a melting point of no less than 2060° C. and which remains in oxide form for at least one of: (i) when exposed to a gas having an oxygen partial pressure of $10^{-15}$ bar, a carbon partial pressure above the carbon partial pressure of the zirconium carbide and zirconium oxide phase transition at the same temperature, and at temperatures below the temperature of the zirconium triple point at the oxygen partial pressure of $10^{-15}$ bar; and (ii) when exposed to a gas having an oxygen partial pressure of $10^{-15}$ bar and at temperatures above the zirconium triple point at the oxygen partial pressure of $10^{-15}$ bar. The refractory material may remain in oxide form when exposed to a gas having an oxygen partial pressure of $10^{-15}$ bar, a carbon partial pressure above the carbon partial pressure of the zirconium carbide and zirconium phase transition at the same temperature, and at temperatures above the zirconium triple point at the oxygen partial pressure of $10^{-15}$ bar; may remain in oxide form when exposed to a gas having carbon partial pressure of $10^{-11}$ bar, an oxygen partial pressure of $10^{-15}$ bar, at a temperature of 2050° C.; may have a melting point of no less than 2160° C.; may remain in the oxide form when exposed to a reference pyrolysis gas mixture having a carbon partial pressure of $10^{-10}$ bar, an oxygen partial pressure of $10^{-15}$ bar, and at a temperature over the full range of from 1800° C. to 2100° C.; may have a crystalline structure that is cubic during heat-up from 1250° C. to 2250° C.; may have a vapor pressure of the refractory material is $\leq 10^{-7}$ bar at 2000° C.; may have at least a first grain mode comprising yttria and a second grain mode comprising yttria; may substantially exclude oxides of toxic ceramics; may include at least one of yttria, another yttrium containing compound, a zirconium containing compound, and combinations thereof; may include from 0.001 wt % to 5 wt % based upon the weight of the refractory material, of compounds that comprise elements selected from the group consisting of Al, Si, Mg, Ca, Fe, Mn, Ni, Co, Cr, Ti, Hf, V, Nb, Ta, Mo, W, Sc, La, and Ce, and mixtures thereof.

Further still, another example, U.S. patent application Ser. No. 12/623,046, which is incorporated by reference, describes a pyrolysis reactor having components or internals, which are exposed to heat within the reactor region, which formed from refractory material in oxide form. These components or internals may be utilized in one or more of the embodiments described above. The refractory material has a melting point of no less than 2060° C. and which remains in oxide form when exposed to a gas having carbon partial pressure of $10^{-22}$ bar and oxygen partial pressure of $10^{-10}$ bar, measured at a temperature of 1200° C., wherein the refractory material has not less than 4 vol % formed porosity, measured at 20° C., based upon the bulk volume of the refractory material; may have a total porosity in the range of from 4 to 60 vol %; may have a formed porosity is determined after sintering at a temperature of not less than 1700° C. for not less than one hour; may have a formed porosity in the range of from 5 to 30 vol %; may have a total porosity in the range of from 5 to 35 vol %; may have a formed porosity that comprises the total of both a formed vacant pore fraction and a formed durable component pore fraction; may include a multimodal grain size distribution including a first grain mode and a second grain mode, the D50 grain size of the first grain mode is not less than three times the D50 grain size of the second grain mode, wherein the formed pores have a D50 diameter in a size range of from not less than the D50 grain size of the second grain mode up to two times the D50 grain size of the first grain mode; may have a formed porosity comprises from 30% to 100% of the total porosity; may have a formed porosity that is created using at least one of a sacrificial voiding agent, a durable voiding agent, and a combination of sacrificial and durable voiding agent, wherein the voiding agent may comprise at least one of a sacrificial polymeric material, a hollow particle, and a solid particle; may have at least 50% of the formed pores have a three-dimensional body factor of not greater than 2.5; may have a melting point of not less than 2160° C.; may remain in the oxide form when exposed to a gas having a carbon partial pressure of $10^{-14}$ bar and oxygen partial pressure of $10^{-10}$ bar, measured at a temperature of 2000° C.; may have a crystalline structure that is cubic during heat-up from 1250° C. to 2250° C.; may have a vapor pressure that is $\leq 10^{-7}$ bar at 2000° C.; may have a thermal shock resistance rating that demonstrates a total crack length per unit area after quenching the reactor component from 1100° C. into a water bath to a temperature of 50° C. is not greater than 30 cm/cm$^2$; may have a modulus of rupture mechanical flexural strength of not less than 13.8 MPa at a temperature in a range of from 1000° C. to 2000° C.; may include at least 50 wt % yttrium oxide (yttria) based upon the total weight of the refractory material; may substantially exclude oxides of toxic ceramics, wherein the oxides of toxic ceramics include beryllium and thorium; may include (i) at least 20 wt % of a first grain mode based upon the total weight of the refractory material, the first grain mode having a D50 grain size in the range of from 5 to 2000 and (ii) at least 1 wt % of second grain mode based upon the total weight of the refractory material, the second grain mode having a D50 grain size in the range of from 0.01 μm up to not greater than one-fourth the D50 grain size of the first grain mode; or may include at least one of yttria, another yttrium containing compound, a zirconium containing compound, and combinations thereof. The formed pores may have a D50 diameter not less than the D50 grain size of the refractory material; may have a D50 diameter in a size range of from not less than the D50 grain size of the refractory material up to five times the D50 grain size of the refractory material; or may have a D50 diameter in a range of from not less than 1.5 times the D50 grain size of the second grain mode up four times the D50 grain size of the second grain mode.

Further, in other embodiments, flue gas from the combustion stage in the reactor may be recycled to the combustion inlet and mixed with air to provide preferred oxygen content in the regeneration-stage feed. Low-oxygen flue gas may also be useable as a purge stage before sending hydrocarbon vapor feed to the reactor in other embodiments.

In yet other embodiments, the process may optionally include separating hydrogen (molecular hydrogen) from the effluent from the reactor to lessen the amount of compression needed downstream of the reactor. That is, the compression of certain reactor effluent components (such as molecular hydrogen) that are not needed in the process downstream of the pyrolysis (e.g., not needed in the recovery stages) may be lessened or eliminated by separating at least a portion of these components from the reactor effluent upstream of one or more of the compression stages. For example, excess hydrogen may be separated as a relatively pure molecular hydrogen stream in certain configurations to further enhance the process. Accordingly, the hydrogen may be separated downstream of the reactor and upstream of additional compression stages for the conversion of the reactor product into ethylene. This hydrogen separation reduces or removes the cost and expense of downstream compression steps, as at least a portion of the hydrogen is removed from the downstream processing.

To provide this hydrogen separation, the reactor effluent may be converted, as noted above. Then, a solids separation process may be utilized followed by hydrogen separation. The hydrogen separation equipment may include one or more membranes, pressure swing adsorption units, and/or combination of these units. Further, the process may include compressing the reactor effluent to a first pressure prior to the separation, and then separating the hydrogen prior to the second compressing step to compress the remaining reactor effluent to a second pressure. The increase in pressure between the compression steps may be ≥5%, ≥10%, ≥15% or even ≥20% based on the lower pressure. This aspect may be further explained in relation to the following examples, which reference FIGS. 3 and 4.

As a first example, the product separation unit 310 or 418 may include two or more membranes and may be utilized to provide the hydrogen separation upstream of the acetylene converter 312 or 424 and downstream of the solid removal unit 306 or 414. In this configuration, the compressor 308 or 416 may be utilized to compress the entire stream from a first pressure to a second pressure, wherein the second pressure is higher than the first pressure. Then, the stream may pass through two or more membrane separation units. The first membrane may remove hydrogen for recycle or sales, while the second membrane may utilize methane as a sweep gas. The use of the methane sweep may then passed to the reactor as fuel or combined with the feed. As a specific example, the first pressure may be 100 psig (689 kPag), which is compressed to a second pressure of 190 psig (1310 kPag) for the hydrogen separation. After a portion of the hydrogen has been removed in the membranes, the remaining stream may be compressed to 230 psig (1586 kPag) in a second compressor upstream of the acetylene converter (such as a vapor phase acetylene converter), while the separated hydrogen may be at 100 psig (689 kPag).

Beneficially, the hydrogen removed from the first membrane may be produced with high purity (e.g., >98%), while the second membrane may be sweep with methane that is utilized within the process. Further, the methane sweep may be utilized to compensate for the pressure drop through the membranes, by providing additional efficiencies to the system.

In an alternative embodiment, a liquid adsorption and desorption unit, utilizing a fluid such as one or more of NMP, DMF, dimethyl formamide (DMF), acetone and other suitable solvents, may be utilized to process the effluent in the liquid phase. The liquid absorption and desorbtion unit may be downstream of the membranes and utilized to separate methane, hydrogen and any ethylene from the effluent to be converted, while the remaining effluent is absorbed and converted in the converter. In this configuration, the compressor 308 or 416 may be utilized to compress the entire stream from a first pressure to a second pressure, wherein the second pressure is higher than the first pressure. Then, the stream may pass through two or more membrane separation units and liquid absorption and desorbtion unit before being compressed in a second compressor. The membrane may operate to remove hydrogen for recycle or sales, but provide the product at a lower pressure than the first pressure. As a specific example, the first pressure may be 30 psig (207 kPag), which is compressed to a second pressure of 120 psig (827 kPag) for the hydrogen separation. After a portion of the hydrogen has been removed in the membranes, which may be at a pressure of 30 psig (207 kPag), the remaining stream may then be passed through the absorber portion of the unit at 110 psig (758 kPag) and the desorbtion portion of the unit at 100 psig (689 kPag). In this embodiment, the removal of the hydrogen upstream of the liquid absorption and desorbtion unit reduces the size of downstream recovery equipment, such as C3 refrigeration units.

In yet another alternative embodiment, the product separation unit 310 or 418 may include one or more membranes in fluid communication with a liquid absorption and desorbtion unit that is disposed between the reactor and other downstream recovery units. The membrane may separate hydrogen from the effluent and the liquid absorption and desorbtion unit may separate methane, hydrogen and any ethylene from the effluent and then convert the acetylene in the stream into ethylene. In this configuration, the compressor 308 or 416 may be utilized to compress the entire stream from a first pressure (e.g., ≥90 psig (621 kPa) or ≥100 psig (689 kPa)) to a second pressure (e.g., ≥160 psig (1103 kPa) or ≥190 psig (1310 kPa)), wherein the second pressure is higher than the first pressure. Then, the stream may pass through one or more membrane separation units and a liquid absorption and desorbtion unit before the remaining stream is compressed in a second compressor. The membrane may operate to remove hydrogen for, e.g., recycle or sales, but provide the product at a lower pressure than the first pressure (e.g., 100 psig (689 kPa)). In this embodiment, the membrane is utilized to removal of the hydrogen upstream of the liquid absorption and desorbtion unit to reduce the size of downstream recovery equipment and compression steps.

In another example, the product separation unit 310 or 418 may include one or more pressure swing adsorption units and may be utilized to provide the hydrogen separation upstream of the acetylene converter 312 or 424 and downstream of the solids removal unit 306 or 414. The pressure swing adsorption unit may be utilized to lessen the pressure drop within the stream. In this configuration, the compressor 308 or 416 may be utilized to compress the entire stream from a first pressure to a second pressure, wherein the second pressure is higher than the first pressure. Then, the stream may pass through the pressure swing adsorption unit to separate hydrogen from the remaining stream before the remaining stream is compressed in a second compressor. The hydrogen may be utilized, e.g., for recycle or sales. As a specific example, the first pressure may be 100 psig (689 kPag), which is compressed to a second pressure of 120 psig (827 kPag) for the hydrogen separation. After a portion of the hydrogen has been removed in the pressure swing adsorption unit, the remaining stream may be compressed to 230 psig (1586 kPag) in a second compressor upstream of the acetylene converter (such as a vapor phase acetylene converter), while the separated hydrogen may be at 100 psig (689 kPag).

In an alternative embodiment, the liquid absorption and desorption unit may be utilized upstream of the pressure swing adsorption unit and utilized to further manage the acetylene in the reactor effluent. In this configuration, the compressor 308 or 416 may be utilized to compress the entire stream from a first pressure to a second pressure, wherein the second pressure is higher than the first pressure. Then, the stream may pass through liquid absorption and desorption unit before being passed to the pressure swing adsorption unit, which is followed by an additional compression step for the remaining stream. The pressure swing adsorption unit may operate to remove hydrogen, e.g., for recycle or sales. As a specific example, the first pressure may be 100 psig (689 kPag), which is compressed to a second pressure of 120 psig (827 kPag) for the liquid absorption and desorption unit. After a portion of the hydrogen, methane and ethylene has been removed in the absorber portion of the unit at pressure of 120 psig (827 kPag) and the desorption portion of the unit at 100 psig (689 kPag), the remaining stream may then be passed through the pressure swing adsorption unit at 100 psig (689 kPag). In this embodiment, the process has enhanced efficiencies by managing the pressure through the steps without having to include additional compression steps.

In other embodiments, acetylene conversion, which may be performed in acetylene converters 312 and 424, may be moved upstream of the compression step to lessen the associated compression steps. This may also benefit any recycle streams removed from the conversion stream, as these separated streams may be at or near the operating pressure of the reactor. Moreover, by maintaining the effluent as one stream with minimal product removal (e.g., the solids and tars), the stream may be maintained below any detonation limits because the process may produce large amounts of hydrogen and other byproducts to dilute other products, such as acetylene. Accordingly, the process may involve having the acetylene hydrogenation unit upstream of any compression steps in the recovery stages of the process.

As an example, the method may include exposing a pyrolysis feed to thermal pyrolysis high-severity operating conditions including a peak pyrolysis gas temperature ≥1200.0° C. or even 1500.0° C. to produce the stream that comprises ethylene, hydrogen and acetylene at a first pressure; and converting at least a portion of the acetylene into an ethylene stream in an acetylene converter located upstream of product stream compression. This method may also include removing from the reactor product a first product comprising tars and/or solids upstream of the converting. As a specific example, the first pressure may be 100 psig (689 kPag), which is reduced to 90 psig (621 kPa) in the reactor and acetylene converter. Then, downstream of conversion, the stream may be compressed to be at 120 psig (827 kPag).

The embodiments of the present techniques may also comprise different embodiments, such as in the following exemplary paragraphs:

1. A hydrocarbon conversion method comprising:
exposing a pyrolysis feed to thermal pyrolysis at a peak pyrolysis gas temperature 1200.0° C. and at a pressure ≥36 psig (248 kPag) to produce a reactor product that comprises $C_2$ unsaturates and has a $C_3^+$ to $C_2$ unsaturate weight ratio ≤0.5.

2. The method of paragraph 1, wherein the $C_3^+$ to acetylene weight ratio is ≤0.45.

3. The method of paragraph 1 or 2, wherein the $C_3^+$ to $C_2$ unsaturate weight ratio is ≤0.4.

4. The method of paragraph 1 or 2, wherein the $C_3^+$ to $C_2$ unsaturate weight ratio is ≤0.3.

5. The method of any one of paragraphs 1 to 4, wherein the reactor product has an ethylene to acetylene weight ratio ≤0.1.

6. The method of any one of paragraphs 1 to 4, wherein the ethylene to acetylene weight ratio is ≥0.5.

7. The method of any one of paragraphs 1 to 6, wherein the pyrolysis feed comprises hydrocarbon, and wherein the pyrolysis feed has a hydrogen ($H_2$) gas to carbon (carbon atoms in feed hydrocarbon molecules) molar ratio in the range of 0.1 to 5.

8. The method of any one of paragraphs 1 to 7, further comprising converting at least a portion of the reactor product into ethylene.

9. The method of paragraph 8, further comprising polymerizing at least a portion of the ethylene.

10. The method of any one of paragraphs 1 to 9, further comprising adjusting the peak pyrolysis gas temperatures and/or the pressure to an optimized value, the optimized value being derived from an optimization function that comprises an ethylene to acetylene weight ratio and the $C_3^+$ to $C_2$ unsaturate weight ratio.

11. The method of paragraph 8 or 9, further comprising compressing at least a portion of the reactor product, the compressing being conducted upstream of the converting.

12. The method of any one of paragraphs 1 to 11, further comprising separating nitrogen from at least a portion of the reactor product.

13. The method of any one of paragraphs 8, 9 and 11, further comprising separating hydrogen from at least a portion of the reactor product, the separating being conducted upstream of the converting.

14. The method of any one of paragraphs 8, 9, 11 and 13, further comprising separating hydrogen downstream of the converting.

15. The method of paragraphs 13 or 14, wherein the hydrogen is separated via one or more of a hydrogen membrane, pressure swing adsorption, electrochemical, cryogenic separation, and solvent absorption.

16. The method of any one of paragraphs 13 to 15, further comprising adding to a combustion feed at least a portion of the separated hydrogen and reacting the combustion feed along with the at least a portion of the separated hydrogen in a thermal pyrolysis reactor to provide heat for the thermal pyrolysis.

17. The method of any one of paragraphs 13 to 15, further comprising deriving the pyrolysis feed from at least a portion of the separated hydrogen.

18. The method of any one of paragraphs 13 to 15, further comprising adding to a combustion feed a first portion of the separated hydrogen to form a mixture and reacting the mixture in a thermal pyrolysis reactor to provide heat for the thermal pyrolysis, wherein the pyrolysis feed is derived from a second portion of the separated hydrogen.

19. The method of any one of paragraphs 13 to 15, further comprising adding to at least a portion of the separated hydrogen at least a portion of the reactor product upstream of the converting.

20. The method of any one of paragraphs 1 to 19, wherein the peak pyrolysis gas temperature is in the range of 1540.0° C. to 2200.0° C., and wherein the exposing is for a residence time in the range from 0.5 seconds to 0.001 seconds.

21. The method of any one of paragraphs 1 to 20, wherein the peak pyrolysis gas temperature is in the range of 1600.0° C. to 1800.0° C., and wherein the exposing is for a residence time in the range from 0.5 seconds to 0.001 seconds.

22. The method of any one of paragraphs 1 to 21, further comprising determining the operating conditions for the thermal pyrolysis to maximize the reactor product's E/A weight ratio at a predetermined $C_3^+$ to $C_2$ unsaturate weight ratio of the reactor product.

23. The method of any one of paragraphs 1 to 15 and 20 to 22, wherein the thermal pyrolysis is performed in a regenerative reverse flow reactor.

24. The method of paragraph 23, wherein the regenerative reverse flow reactor comprises a reactor body, wherein the reactor body forms a reaction region within the reactor body; a packing material disposed at least partially within the reaction region; and one or more poppet valve assemblies coupled to the reactor body and in flow communication with the reaction region and controlling fluid flow of the at least a portion of the pyrolysis feed between a location external to the reactor body and within the reaction region.

25. The method of paragraphs 23 or 24, further comprising: exothermically reacting a first combustion feed with a second combustion feed to heat a region at least partially within the regenerative reverse flow reactor; removing combustion products from the regenerative reverse flow reactor; and heating the pyrolysis feed using at least a portion of the heat generated by the exothermic reaction.

26. The method of paragraph 25, further comprising purging the heated region with a vapor purge stream after the removing the combustion products and prior to passing the at least a portion of the pyrolysis feed into the heated region.

27. The method of paragraphs 25 or 26, wherein the first combustion feed and the second combustion feed are separately heated within the regenerative reverse flow reactor prior to exothermically reacting in the region.

28. The method of any one of paragraphs 1 to 27, further comprising deriving the pyrolysis feed and bottoms product from a hydrocarbon feed prior to the exposing.

29. The method of paragraph 28, wherein the hydrocarbon feed comprises crude oil and/or crude oil components.

30. The method of any one of paragraphs 1 to 28, wherein the pyrolysis feed comprises substantially methane.

31. The method of any one of paragraphs 23 to 27, wherein the combustion and pyrolysis are conducted in sequence, the sequence having a cycle time in the range of from 0.5 second to 30 seconds.

32. The method of any one of paragraphs 1 to 31, wherein the pressure is in the range of 44 psig (303 kPag) to 300 psig (2068 kPag).

33. The method of any one of paragraphs 1 to 31, wherein the pressure is in the range of 103 psig (710 kPag) to 163 psig (1124 kPag).

34. The method of any one of paragraphs 23 to 27, further comprising quenching the reactor product, the quenching being conducted within the regenerative reverse flow reactor in the absence of any added fluid.

35. An apparatus for processing hydrocarbons comprising: a thermal pyrolysis reactor configured to expose at least a portion of a pyrolysis feed to a peak pyrolysis gas temperature ≥1540.0° C. at a pressure ≥36 psig (248 kPag) within the thermal pyrolysis reactor to produce a reactor product comprising ethylene and acetylene and has a $C_3^+$ to $C_2$ unsaturate weight ratio ≤0.5; a solids removal unit in fluid communication with the thermal pyrolysis reactor and configured to separate a bottoms product comprising tars and/or solids from at least a portion of the reactor product.

36. The apparatus of paragraph 35, further comprising a converter in fluid communication with the solids removal unit, the converter being configured to convert the at least a portion of the reactor product into a conversion product.

37. The apparatus of paragraph 36, further comprising a polymerization unit in fluid communication with the converter, the polymerization unit being configured to convert at least a portion of the conversion product into polyethylene.

38. The apparatus of any one of paragraphs 35 to 37, further comprising a compressor in fluid communication with the solid removal unit, the compressor being configured to compress the at least a portion of the reactor product.

39. The apparatus of any one of paragraphs 36 to 38, further comprising a nitrogen separation unit in fluid communication with the converter, the nitrogen separation unit being configured to separate nitrogen from the at least a portion of the reactor product.

40. The apparatus of any one of paragraphs 36 to 39, further comprising a product separation unit in fluid communication with the converter, the product separation unit being configured to separate a hydrogen product from the at least a portion of the reactor product prior to the converter.

41. The apparatus of any one of paragraphs 36 to 39, further comprising a product separation unit in fluid communication with the converter, the product separation unit being configured to separate a hydrogen product from the conversion product.

42. The apparatus of any one of paragraphs 40 to 41, wherein the product separation unit comprises at least one of a membrane, a pressure swing adsorption unit, an electrochemical unit, a cryogenic separation unit, a solvent absorption unit and any combination thereof.

43. The apparatus of any one of paragraphs 40 to 42, further comprising one or more lines providing fluid communication between the product separation unit and the thermal pyrolysis reactor, at least one of the lines being configured to provide a portion of the hydrogen product to a combustion feed being provided to the thermal pyrolysis reactor, wherein the thermal pyrolysis reactor is configured to react the portion of the hydrogen product and the combustion feed to heat the thermal pyrolysis reactor.

44. The apparatus of any one of paragraphs 40 to 42, further comprising one or more lines providing fluid communication between the product separation unit and the thermal pyrolysis reactor, at least one of the lines being configured to combine a portion of the hydrogen product with the pyrolysis feed prior to heating the pyrolysis feed in the thermal pyrolysis unit.

45. The apparatus of any one of paragraphs 40 to 42, further comprising (i) one or more lines providing fluid communication between the hydrogen separation unit and the thermal pyrolysis reactor, at least one of the lines being configured to provide a first portion of the hydrogen product to a combustion feed being provided to the thermal pyrolysis reactor and (ii) one or more lines providing fluid communication between the hydrogen separation unit and the thermal pyrolysis reactor, at least one of the lines being configured to provide a second portion of the hydrogen product to the pyrolysis feed prior to heating the pyrolysis feed in the thermal pyrolysis unit.

46. The apparatus of any one of paragraphs 35 to 45, wherein the thermal pyrolysis reactor is configured to expose the pyrolysis feed to the peak pyrolysis gas temperatures from 1540.0° C. to 2200.0° C., and maintain the pyrolysis feed within the thermal pyrolysis reactor for a residence time in the range of 0.5 seconds to 0.001 seconds.

47. The apparatus of any one of paragraphs 35 to 45, wherein the thermal pyrolysis reactor is configured to expose the pyrolysis feed to the peak pyrolysis gas temperatures from 1600.0° C. to 1800.0° C., and maintain the pyrolysis feed within the thermal pyrolysis reactor for a residence time in the range of 0.5 seconds to 0.001 seconds.

48. The apparatus of any one of paragraphs 35 to 47, wherein the thermal pyrolysis reactor is a regenerative reverse flow reactor that comprises: a reactor body, wherein the reactor body forms a reaction region within the reactor body; a packing material disposed at least partially within the reaction region; and one or more valve assemblies coupled to the reactor body and in flow communication with the reaction region and configured to control fluid flow of the at least a portion of the pyrolysis feed between a location external to the reactor body and within the reaction region.

49. The apparatus of any one of paragraphs 35 to 47, wherein the one or more valve assemblies comprise one or more poppet valve assemblies.

50. The apparatus of any one of paragraphs 35 to 49, further comprising a feed separation unit in fluid communication with the thermal pyrolysis reactor, the feed separation unit being configured to separate a hydrocarbon feed into a reactor feed and bottoms product, wherein the pyrolysis feed is derived from the reactor feed.

51. The apparatus of any one of paragraphs 35 to 50, wherein the thermal pyrolysis reactor is configured to expose the at least a portion of the pyrolysis feed to pressure ≥44 psig (303 kPag) and ≤300 psig (2068 kPag).

52. The apparatus of any one of paragraphs 35 to 50, wherein the thermal pyrolysis reactor is configured to expose the at least a portion of the pyrolysis feed to pressure ≥103 psig (710 kPag) and ≤163 psig (1124 kPag).

53. The method of any of paragraphs 1 to 34, further comprising: compressing at least a portion of the reactor product from a first pressure to a second pressure, wherein the second pressure is higher than the first pressure; removing hydrogen from the compressed reactor product; compressing the remaining reactor product from the second pressure to a third pressure, wherein the third pressure is higher than the second pressure; and converting at least a portion of the acetylene in the remaining reactor product into a final product.

54. The method of paragraph 53, wherein the removing is performed with two or more membranes coupled in series, wherein the second membrane utilizes a light hydrocarbon stream to sweep the hydrogen from the membrane.

While the present invention has been described and illustrated with respect to certain embodiments, it is to be understood that the invention is not limited to the particulars disclosed and extends to all equivalents within the scope of the claims.

The invention claimed is:

1. A hydrocarbon conversion method comprising: exposing a pyrolysis feed comprising hydrocarbons and an added diluent in a regenerative reverse-flow thermal pyrolysis reactor to thermal pyrolysis conditions at a peak pyrolysis gas temperature ≥1200.0° C., for a residence time in the range of 4 milliseconds to 50 milliseconds, and at a pressure ≥44 psig to produce a reactor product comprising $C_2$ unsaturates and having a $C_{3+}$ to $C_2$ unsaturates weight ratio ≤0.5, wherein (i) the added diluent is added in an amount of more than zero but up to 10 wt % based on the combined weight of the hydrocarbons and the added diluent and (ii) the added diluent is one or more of $H_2O$, $CO_2$, and $H_2S$.

2. The method of claim 1, wherein the reactor product has a $C_{3+}$ to C2 to acetylene weight ratio ≤0.45.

3. The method of claim 1, wherein the reactor product has an ethylene to acetylene weight ratio ≥0.5, and the peak pyrolysis gas temperature is in a range of from 1540.0° C. to 2200.0° C.

4. The method of claim 1, wherein the pyrolysis feed has a molar ratio of hydrogen gas to carbon atoms in the hydrocarbons in the pyrolysis feed in the range of 0.1 to 5.

5. The method of claim 1, further comprising converting at least a portion of the reactor product into ethylene.

6. The method of claim 5, further comprising polymerizing at least a portion of the ethylene.

7. The method of claim 5, further comprising compressing at least a portion of the reactor product, the compressing being conducted upstream of the converting.

8. The method of claim 5, further comprising separating hydrogen from at least a portion of the reactor product, the separating being conducted upstream of the converting.

9. The method of claim 5, further comprising separating hydrogen downstream of the converting.

10. The method of claim 8, further comprising adding to a combustion feed at least a portion of the separated hydrogen and reacting the combustion feed along with the at least a portion of the separated hydrogen during reverse flow in the regenerative reverse-flow thermal pyrolysis reactor to provide heat for the thermal pyrolysis.

11. The method of claim 8, further comprising deriving the pyrolysis feed from at least a portion of the separated hydrogen.

12. The method of claim 8, further comprising adding to a combustion feed a first portion of the separated hydrogen to form a mixture and reacting the mixture during reverse flow in the regenerative reverse-flow thermal pyrolysis reactor to provide heat for the thermal pyrolysis, wherein the pyrolysis feed is derived from a second portion of the separated hydrogen.

13. The method of claim 1, wherein the peak pyrolysis gas temperature is in the range of 1600.0° C. to 1800.0° C.

14. The method of claim 1, wherein the reactor product comprises ethylene and acetylene, the method further comprising determining the thermal pyrolysis conditions for the thermal pyrolysis to maximize the reactor product's E/A weight ratio.

15. The method of claim 1, wherein the pressure is in the range of 44 psig to 300 psig.

16. The method of claim 1, wherein the pressure is in the range of from 103 psig to 300 psig.

* * * * *